US012345545B2

(12) United States Patent
Tanaka et al.

(10) Patent No.: US 12,345,545 B2
(45) Date of Patent: Jul. 1, 2025

(54) TRAVEL DISTANCE CALCULATION METHOD, TRAVEL DISTANCE CALCULATION DEVICE, AND NON-TRANSITORY COMPUTER READABLE RECORDING MEDIUM STORING TRAVEL DISTANCE CALCULATION PROGRAM

(71) Applicant: Panasonic Intellectual Property Corporation of America, Torrance, CA (US)

(72) Inventors: Hiroya Tanaka, Osaka (JP); Yuko Kida, Osaka (JP)

(73) Assignee: Panasonic Intellectual Property Corporation of America, Torrance, CA (US)

( * ) Notice: Subject to any disclaimer, the term of this patent is extended or adjusted under 35 U.S.C. 154(b) by 408 days.

(21) Appl. No.: 17/900,591

(22) Filed: Aug. 31, 2022

(65) Prior Publication Data

US 2022/0412773 A1   Dec. 29, 2022

Related U.S. Application Data

(63) Continuation of application No. PCT/JP2021/002466, filed on Jan. 25, 2021.
(Continued)

(30) Foreign Application Priority Data

Dec. 15, 2020   (JP) .................................. 2020-207580

(51) Int. Cl.
*G01C 22/00* (2006.01)
*A61B 5/11* (2006.01)

(52) U.S. Cl.
CPC ............ *G01C 22/00* (2013.01); *A61B 5/1113* (2013.01)

(58) Field of Classification Search
CPC ....................................................... G01C 22/00
See application file for complete search history.

(56) References Cited

U.S. PATENT DOCUMENTS

2004/0183667 A1    9/2004    Nicoletti et al.

FOREIGN PATENT DOCUMENTS

| EP | 3220326 | 9/2017 |
| JP | 2008-099843 | 5/2008 |
| JP | 2017-164462 | 9/2017 |

OTHER PUBLICATIONS

Machine translation of JP2008099843 (Year: 2008).*
(Continued)

*Primary Examiner* — Walter L Lindsay, Jr.
*Assistant Examiner* — Andrew V Do
(74) *Attorney, Agent, or Firm* — Greenblum and Bernstein, P.L.C.

(57) ABSTRACT

A travel distance calculation device is configured to: add a first distance between a first main sensor and a hub sensor to a travel distance when a person is detected by the hub sensor provided in a third space connecting a first space and a second space after the person is detected by the first main sensor provided in the first space; add a second distance between a second main sensor and the hub sensor to the travel distance when the person is detected by the hub sensor after the person is detected by the second main sensor provided in the second space; and add no third distance between the first main sensor and the second main sensor to the travel distance when the person is detected by the second main sensor after the person is detected by the first main sensor.

5 Claims, 18 Drawing Sheets

Related U.S. Application Data

(60) Provisional application No. 62/990,250, filed on Mar. 16, 2020.

(56) References Cited

OTHER PUBLICATIONS

International Search Report (ISR) from International Searching Authority (Japan Patent Office) in International Pat. Appl. No. PCT/JP2021/002466, dated Mar. 9, 2021, together with an English language translation.

\* cited by examiner

FIG.3

| CORRIDOR | DINING ROOM | 4 METERS |
| --- | --- | --- |
| | LIVING ROOM | 4 METERS |
| | BEDROOM | 3 METERS |
| | WESTERN-STYLE ROOM | 3 METERS |
| | STOREROOM | 3 METERS |
| | TOILET | 2 METERS |
| | WASHROOM | 3 METERS |
| | ENTRANCE | 6 METERS |

FIG.11

| CORRIDOR | DINING ROOM (ENTRANCE) | 4 METERS |
|---|---|---|
| | LIVING ROOM (ENTRANCE) | 4 METERS |
| | BEDROOM | 3 METERS |
| | WESTERN-STYLE ROOM | 3 METERS |
| | STOREROOM | 3 METERS |
| | TOILET | 2 METERS |
| | WASHROOM | 3 METERS |
| | ENTRANCE | 6 METERS |
| DINING ROOM (ENTRANCE) | TABLE | 6 METERS |
| | REFRIGERATOR | 9 METERS |
| | MICROWAVE OVEN | 3 METERS |
| | KITCHEN | 5 METERS |
| TABLE | REFRIGERATOR | 2 METERS |
| | MICROWAVE OVEN | 2 METERS |
| | KITCHEN | 3 METERS |
| REFRIGERATOR | MICROWAVE OVEN | 4 METERS |
| | KITCHEN | 1 METER |
| MICROWAVE OVEN | KITCHEN | 1 METER |
| LIVING ROOM (ENTRANCE) | SOFA | 5 METERS |

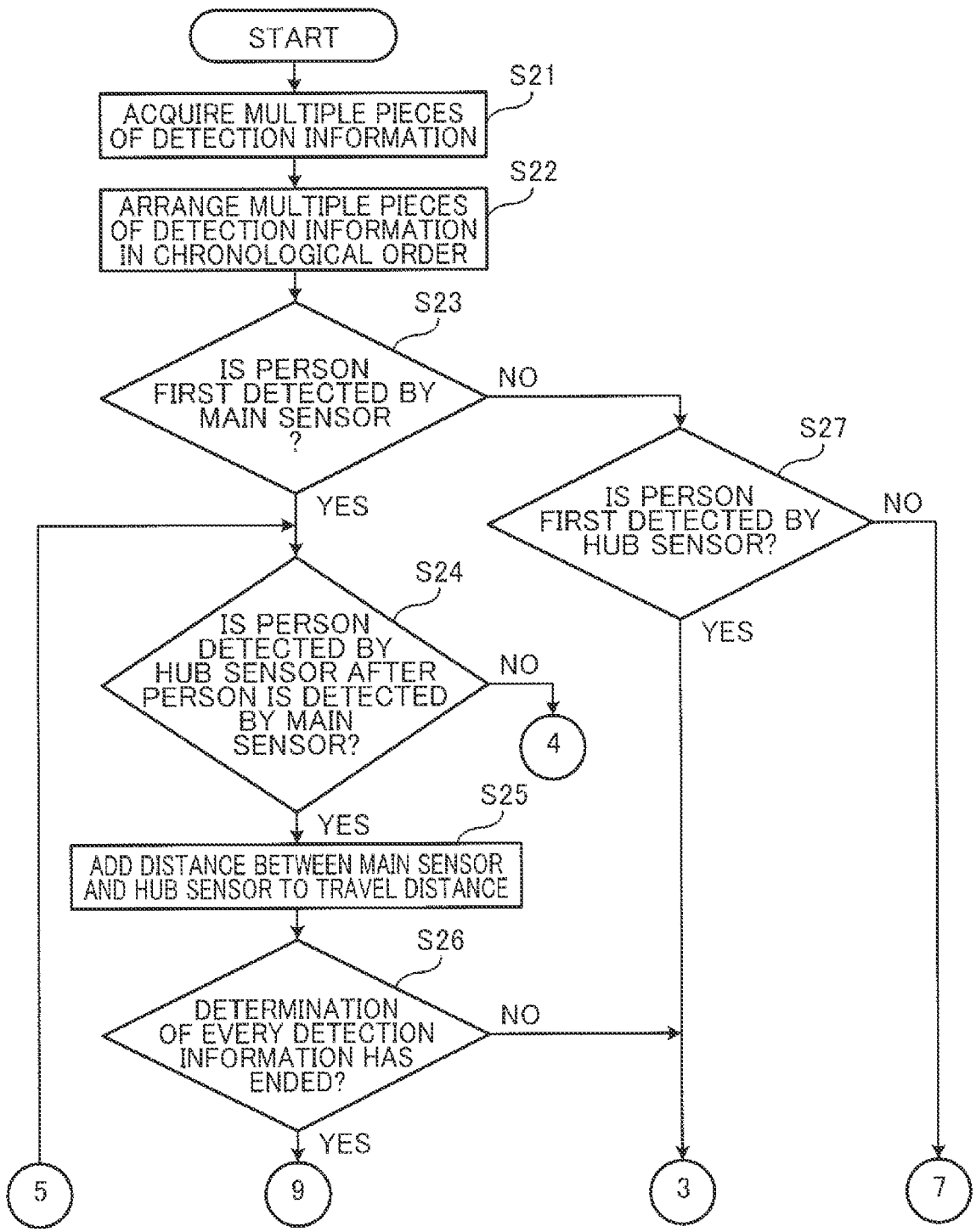

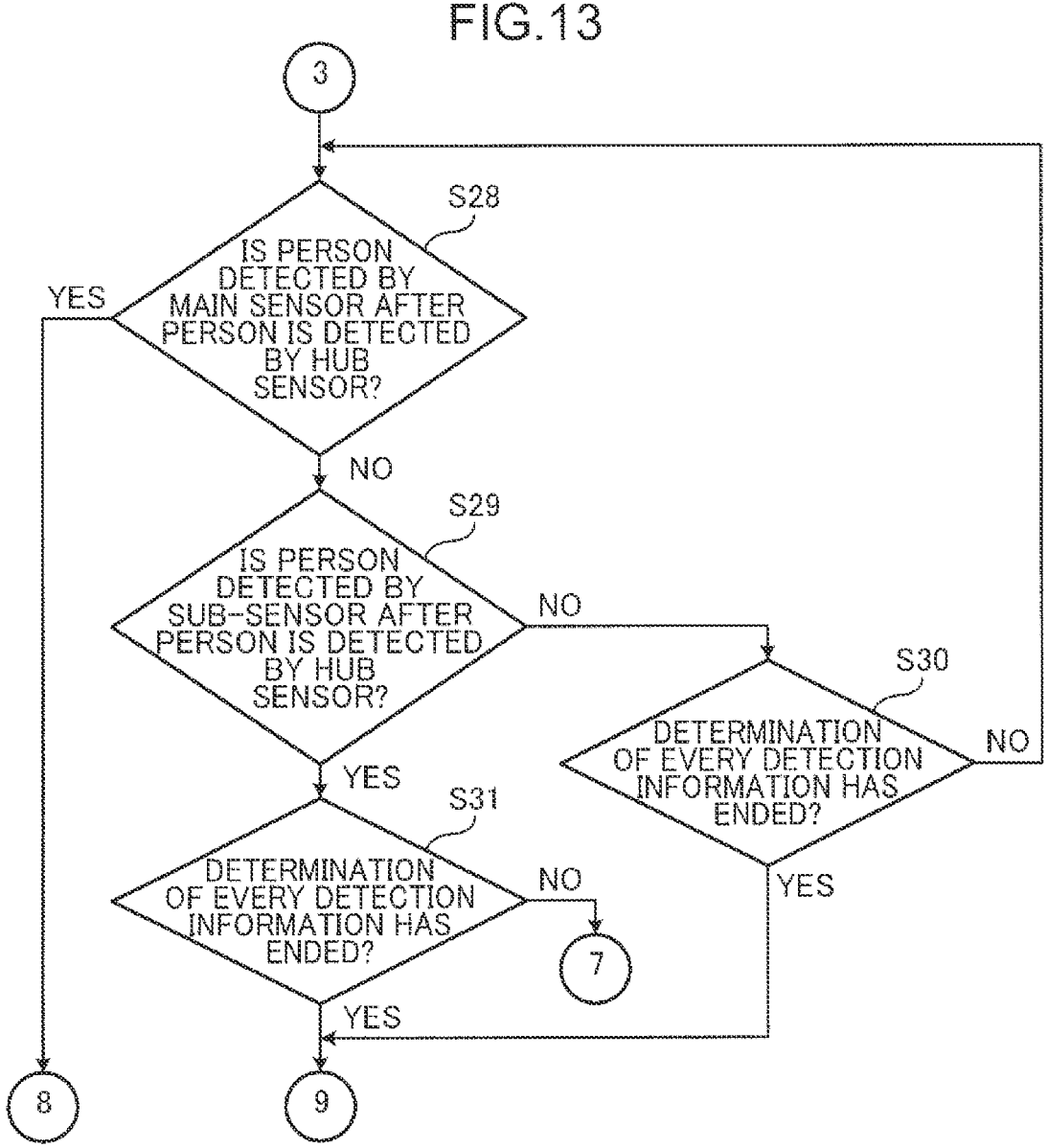

TRAVEL DISTANCE CALCULATION METHOD, TRAVEL DISTANCE CALCULATION DEVICE, AND NON-TRANSITORY COMPUTER READABLE RECORDING MEDIUM STORING TRAVEL DISTANCE CALCULATION PROGRAM

TECHNICAL FIELD

The present disclosure relates to a technique for calculating a travel distance of a person in a house.

BACKGROUND ART

Care receivers living alone tend to have a reduced opportunity to go out and a reduced amount of physical activity and exercise. The decrease in amount of physical activity and exercise affects various life behaviors such as eating and drinking, sleeping, and excretion. Thus, caregivers and care managers measure the amount of activity of care receivers to help to assist life of the care receivers.

To measure the amount of activity in daily life, the care receivers themselves need to wear activity meters. However, the care receivers may forget to wear the activity meters or the care receivers may not wear the activity meters due to troublesome operation, so that it is difficult to accurately measure the amount of activity.

Thus, a technique for measuring the amount of activity without attaching an activity meter to a care receiver has been developed.

For example, Patent Literature 1 discloses a technique in which the amount of indoor exercise of a human body is calculated using human body position information sensed by multiple passive sensors installed for each indoor room and disposed at regular intervals at positions on a vertical axis and a horizontal axis in plan view of the room.

Unfortunately, the above-described conventional technique does not consider erroneous reaction of the sensors, and thus further improvement is required.

CITATION LIST

Patent Literature

Patent Literature 1: JP 2008-99843 A

SUMMARY OF INVENTION

The present disclosure has been made to solve the above problem, and an object of the present disclosure is to provide a technique capable of calculating a travel distance of a person even when a sensor reacts erroneously.

A travel distance calculation method according to an aspect of the present disclosure is used in a travel distance calculation device that calculates a travel distance of a person in a house, the method including: acquiring first detection information indicating that the person is detected by a first sensor provided in a first space in the house, second detection information indicating that the person is detected by a second sensor provided in a second space different from the first space in the house, and third detection information indicating that the person is detected by a third sensor provided in a third space connecting the first space and the second space in the house; adding a first distance between the first sensor and the third sensor to the travel distance based on the first detection information and the third detection information when the person is detected by the third sensor after the person is detected by the first sensor or when the person is detected by the first sensor after the person is detected by the third sensor, adding a second distance between the second sensor and the third sensor to the travel distance based on the second detection information and the third detection information when the person is detected by the third sensor after the person is detected by the second sensor or when the person is detected by the second sensor after the person is detected by the third sensor, and adding no third distance between the first sensor and the second sensor to the travel distance based on the first detection information and the second detection information when the person is detected by the second sensor after the person is detected by the first sensor or when the person is detected by the first sensor after the person is detected by the second sensor; and outputting the added travel distance.

The present disclosure enables calculating a travel distance of a person even when a sensor reacts erroneously.

BRIEF DESCRIPTION OF DRAWINGS

FIG. 3 is a diagram illustrating an example of a distance table stored in a distance table storage in the first embodiment.

FIG. 11 is a diagram illustrating an example of a distance table stored in a distance table storage in the second embodiment.

FIG. 12 is a first flowchart for illustrating travel distance calculation processing in a travel distance calculation device according to the second embodiment of the present disclosure.

FIG. 13 is a second flowchart for illustrating travel distance calculation processing in the travel distance calculation device according to the second embodiment of the present disclosure.

Figure 1:
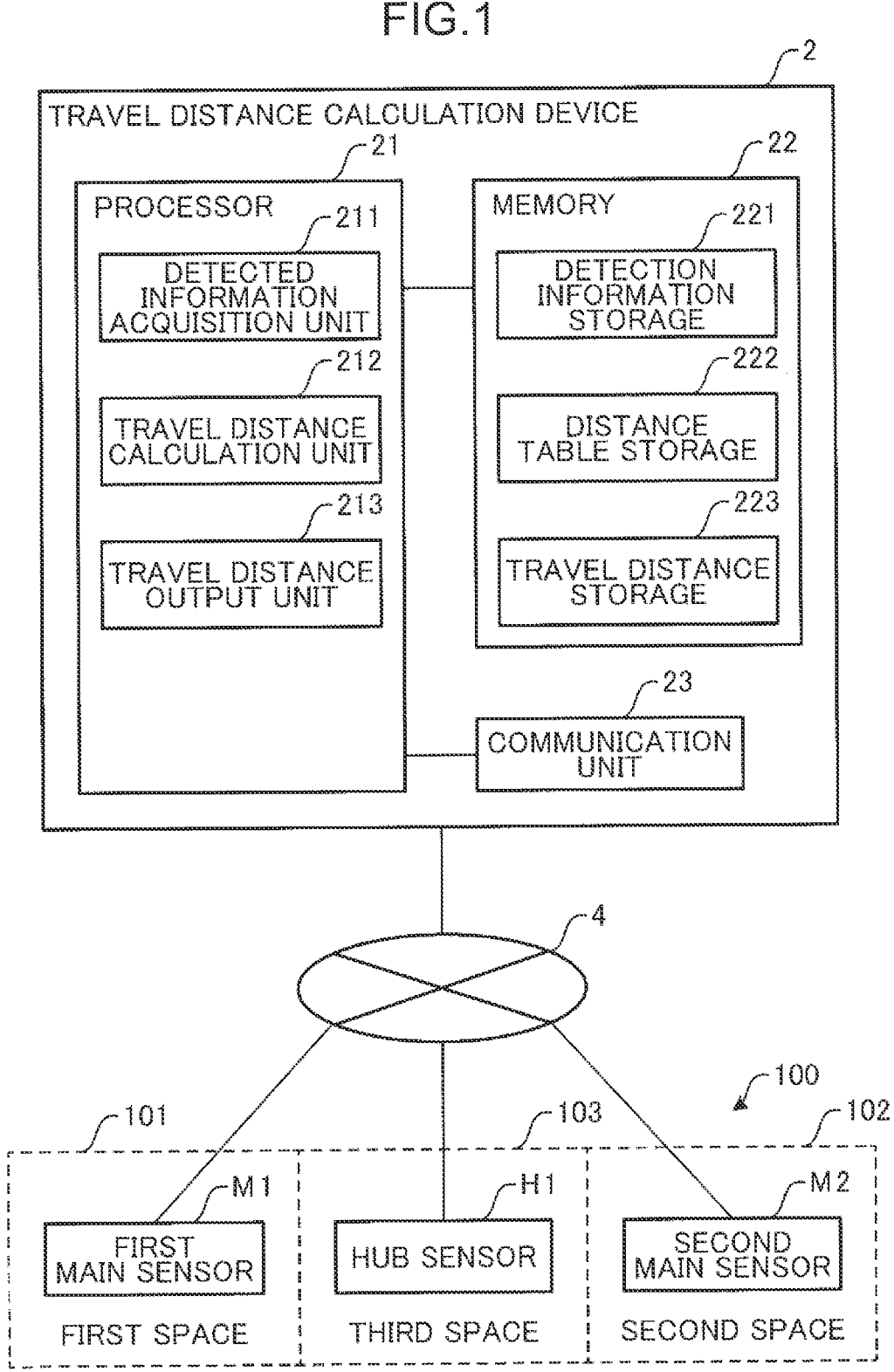
FIG. 1 is a block diagram illustrating a configuration of a travel distance calculation system according to a first embodiment of the present disclosure.

DESCRIPTION OF EMBODIMENTS (Underlying Knowledge of Present Disclosure)

The conventional technique described above does not consider erroneous reaction of a sensor, and thus has difficulty in calculating a travel distance of a person when the sensor reacts erroneously.

The conventional technique described above also requires multiple sensors for each indoor room, and thus requires cost for installing the multiple sensors. The conventional technique particularly focuses on capturing activity of a person in a room by installing multiple sensors in one space serving as the room. Thus, travel of a relatively short distance is conventionally measured. However, measuring a relatively long distance such as travel between indoor rooms causes a problem that a large cost is required for installing multiple sensors.

To solve the above problem, a travel distance calculation method according to an aspect of the present disclosure is used in a travel distance calculation device that calculates a travel distance of a person in a house, the method including: acquiring first detection information indicating that the person is detected by a first sensor provided in a first space in the house, second detection information indicating that the person is detected by a second sensor provided in a second space different from the first space in the house, and third detection information indicating that the person is detected by a third sensor provided in a third space connecting the first space and the second space in the house; adding a first distance between the first sensor and the third sensor to the travel distance based on the first detection information and the third detection information when the person is detected by the third sensor after the person is detected by the first sensor or when the person is detected by the first sensor after the person is detected by the third sensor, adding a second distance between the second sensor and the third sensor to the travel distance based on the second detection information and the third detection information when the person is detected by the third sensor after the person is detected by the second sensor or when the person is detected by the second sensor after the person is detected by the third sensor, and adding no third distance between the first sensor and the second sensor to the travel distance based on the first detection information and the second detection information when the person is detected by the second sensor after the person is detected by the first sensor or when the person is detected by the first sensor after the person is detected by the second sensor; and outputting the added travel distance.

According to this configuration, a person cannot travel from the first space to the second space without passing through the third space connecting the first space and the second space in the house. Thus, when the third sensor provided in the third space detects a person after the first sensor provided in the first space detects the person, or when the first sensor provided in the first space detects the person after the third sensor provided in the third space detects the person, the first distance between the first sensor and the third sensor is added to a travel distance. When the third sensor provided in the third space detects the person after the second sensor provided in the second space detects the person, or when the second sensor provided in the second space detects the person after the third sensor provided in the third space detects the person, the second distance between the second sensor and the third sensor is added to the travel distance. When the second sensor provided in the second space detects the person after the first sensor provided in the first space detects the person, or when the first sensor provided in the first space detects the person after the second sensor provided in the second space detects the person, the third distance between the first sensor and the second sensor is not added to the travel distance.

Thus, when the second sensor provided in the second space detects the person after the first sensor provided in the first space detects the person, for example, the third distance between the first sensor and the second sensor is not added to the travel distance because the person has not passed through the third space and a flow line of the person is not correctly captured. Thus, the distance between the sensors is added to the travel distance in consideration of the flow line of the person, so that the travel distance of the person can be calculated even when the sensors react erroneously.

The first space, the second space, and the third space are respectively provided with the first sensor, the second sensor, and the third sensor one by one, so that multiple sensors are not required for each space, and thus enabling reduction in cost for installing the multiple sensors. Additionally, relatively long travel such as travel between spaces in a house can be captured at low cost.

The travel distance calculation method described above may be configured such that when the person is detected by the third sensor after the person is detected by the first sensor or when the person is detected by the first sensor after the person is detected by the third sensor, the first distance associated with a first combination of an installation location of the first sensor and an installation location of the third sensor is read out from a table to add the first distance to the travel distance, the table being configured to associate the first combination of the installation location of the first sensor and the installation location of the third sensor with the first distance between the first sensor and the third sensor, and a second combination of an installation location of the second sensor and the installation location of the third sensor with the second distance between the second sensor and the third sensor, and when the person is detected by the third sensor after the person is detected by the second sensor or when the person is detected by the second sensor after the person is detected by the third sensor, the second distance associated with the second combination of the installation location of the second sensor and the installation location of the third sensor is read out from the table to add the second distance to the travel distance.

This configuration includes the table in which a combination of installation locations of two sensors is associated with a distance between the two sensors. Thus, when a distance associated with the combination of the installation locations of the two sensors is read out from the table, a distance traveled by the person can be easily calculated.

The table may be configured such that a third combination of the installation location of the first sensor and the installation location of the second sensor is not associated with the third distance between the first sensor and the second sensor. In this case, even when the second sensor detects the person after the first sensor detects the person, the table does not include the third distance associated with the third combination of the installation location of the first sensor and the installation location of the second sensor, so that the third distance cannot be read out from the table. Thus, only a distance associated with the table is added to the travel distance, so that processing of adding a distance between sensors to the travel distance can be reduced.

The travel distance calculation method described above may further include acquiring fourth detection information indicating that the person is detected by a fourth sensor provided at a position different from a position where the first sensor is provided in the first space, wherein when the person is detected by the fourth sensor after the person is detected by the first sensor or when the person is detected by the first sensor after the person is detected by the fourth sensor, a fourth distance between the first sensor and the fourth sensor is added to the travel distance based on the first detection information and the fourth detection information.

This configuration provides the first sensor, and the fourth sensor at a position different from the position where the first sensor is provided in the first space, and enables calculating a more accurate travel distance of the person by adding the fourth distance between the first sensor and the fourth sensor in the first space to the travel distance.

The travel distance calculation method described above may be configured such that when the person is detected by the second sensor after the person is detected by the third sensor, the person is detected by the first sensor after the person is detected by the second sensor, and the person is detected continuously three or more times by at least one of the first sensor and the fourth sensor after the person is detected by the first sensor, the first distance between the first sensor and the third sensor is added to the travel distance without adding the second distance between the second sensor and the third sensor to the travel distance.

According to this configuration, when the person is detected continuously three or more times by at least one of the first sensor and the fourth sensor after the person is sensed by the first sensor, the person is estimated to be in the first space. Thus, when the second sensor detects the person after the third sensor detects the person, the first sensor detects the person after the second sensor detects the person, and at least one of the first sensor and the fourth sensor continuously detects the person three or more times after the first sensor detects the person, it can be estimated that the second sensor has reacted erroneously, and that the person has traveled from the third space to the first space instead of traveling from the third space to the second space. As a result, the travel distance of the person can be calculated more accurately even when a sensor reacts erroneously.

The travel distance calculation method described above may be configured such that the travel distance is not calculated when the person is detected simultaneously by any two of the first sensor, the second sensor, and the third sensor.

When multiple persons are in the house, it is difficult to calculate a travel distance of only a subject for which a travel distance is to be calculated. Thus, when any two of the first sensor, the second sensor, and the third sensor detect the person simultaneously, the calculation of the travel distance may be stopped. This configuration causes no travel distance to be calculated when a person other than the subject for which a travel distance is to be calculated is in the house, and thus enabling calculation of the travel distance of only the subject.

The present disclosure can be implemented not only as the travel distance calculation method for performing characteristic processing as described above, but also as a travel distance calculation device or the like having a characteristic configuration corresponding to a characteristic method performed according to the travel distance calculation method. The present disclosure can also be implemented as a computer program that causes a computer to execute characteristic processing included the travel distance calculation method described above. Thus, even other aspects below can achieve an effect as in the travel distance calculation method described above.

A travel distance calculation device according to another aspect of the present disclosure calculates a travel distance of a person in a house, the device including: an acquisition unit that acquires first detection information indicating that the person is detected by a first sensor provided in a first space in the house, second detection information indicating that the person is detected by a second sensor provided in a second space different from the first space in the house, and third detection information indicating that the person is detected by a third sensor provided in a third space connecting the first space and the second space in the house; a travel distance calculation unit that adds a first distance between the first sensor and the third sensor to the travel distance based on the first detection information and the third detection information when the person is detected by the third sensor after the person is detected by the first sensor or when the person is detected by the first sensor after the person is detected by the third sensor, and that adds a second distance between the second sensor and the third sensor to the travel distance based on the second detection information and the third detection information when the person is detected by the third sensor after the person is detected by the second sensor or when the person is detected by the second sensor after the person is detected by the third sensor, and that adds no third distance between the first sensor and the second sensor to the travel distance based on the first detection information and the second detection information when the person is detected by the second sensor after the person is detected by the first sensor or when the person is detected by the first sensor after the person is detected by the second sensor; and an output unit that outputs the added travel distance.

A non-transitory computer readable recording medium storing a travel distance calculation program according to yet another aspect of the present disclosure is configured to calculate a travel distance of a person in a house, the program causing a computer to function so as to: acquire first detection information indicating that the person is detected by a first sensor provided in a first space in the house, second detection information indicating that the person is detected by a second sensor provided in a second space different from the first space in the house, and third detection information indicating that the person is detected by a third sensor provided in a third space connecting the first space and the second space in the house; add a first distance between the first sensor and the third sensor to the travel distance based on the first detection information and the third detection information when the person is detected by the third sensor after the person is detected by the first sensor or when the person is detected by the first sensor after the person is detected by the third sensor, add a second distance between the second sensor and the third sensor to the travel distance based on the second detection information and the third detection information when the person is detected by the third sensor after the person is detected by the second sensor or when the person is detected by the second sensor after the person is detected by the third sensor, and add no third distance between the first sensor and the second sensor to the travel distance based on the first detection information and the second detection information when the person is detected by the second sensor after the person is detected by the first sensor or when the person is detected by the first sensor after the person is detected by the second sensor; and output the added travel distance.

Hereinafter, embodiments of the present disclosure will be described with reference to the accompanying drawings. The following embodiments are merely examples embodying the present disclosure, and do not limit the technical scope of the present disclosure.

First Embodiment

FIG. 1 is a block diagram illustrating a configuration of a travel distance calculation system according to a first embodiment of the present disclosure.

The travel distance calculation system illustrated in FIG. 1 includes a first main sensor M1, a second main sensor M2, a hub sensor H1, and a travel distance calculation device 2.

The first main sensor M1 is provided in a first space 101 in a house 100 to detect a person in the first space 101. The first main sensor M1 is a motion sensor or a door opening-closing sensor provided at an entrance of the first space 101, for example. The first space 101 is a room in the house 100, such as a living room, a dining room, a bedroom, a toilet, or a washroom, for example. When detecting a person in the first space 101, the first main sensor M1 transmits first detection information indicating that the person is detected to the travel distance calculation device 2. The first detection information includes time information indicating time at which the person is detected.

The second main sensor M2 is provided in a second space 102 different from the first space 101 in the house 100 to detect a person in the second space 102. The second main sensor M2 is a motion sensor or a door opening-closing sensor provided at an entrance of the second space 102, for example. The second space 102 is a room in the house 100, such as the living room, the dining room, the bedroom, the toilet, or the washroom, for example. When detecting a person in the second space 102, the second main sensor M2 transmits second detection information indicating that the person is detected to the travel distance calculation device 2. The second detection information includes time information indicating time at which the person is detected.

The hub sensor H1 is provided in a third space 103 connecting the first space 101 and the second space 102 in the house 100 to detect a person in the third space 103. The hub sensor H1 is a motion sensor, for example. The third space 103 is a corridor, for example, and is a place through which a person passes when traveling between the first space 101 and the second space 102. When detecting a person in the third space 103, the hub sensor H1 transmits third detection information indicating that the person is detected to the travel distance calculation device 2. The third detection information includes time information indicating time at which the person is detected.

The first main sensor M1 is an example of a first sensor, the second main sensor M2 is an example of a second sensor, and the hub sensor H1 is an example of a third sensor.

Although the house 100 illustrated in FIG. 1 includes the first space 101, the second space 102, and the third space 103, the present disclosure is not particularly limited thereto and may include four or more spaces. Each of the four or more spaces may be provided with a main sensor or a hub sensor. Each space is provided with any one of the main sensor and the hub sensor.

The third space may be provided with multiple hub sensors H1. This is effective when the third space is too wide for one hub sensor H1 to detect a person in the third space. The hub sensor H1 is installed in a place that is not limited to the corridor, and the hub sensor H1 may be installed in a room through which a person frequently passes. The hub sensor H1 may be installed in each of multiple spaces.

The travel distance calculation device 2 calculates a travel distance of a person in the house 100. The travel distance calculation device 2 is a server, for example. The travel distance calculation device 2 is communicably connected to each of the first main sensor M1, the second main sensor M2, and the hub sensor H1 via a network 4. The network 4 is the Internet, for example.

The travel distance calculation device 2 includes a processor 21, a memory 22, and a communication unit 23.

The communication unit 23 receives the first detection information transmitted by the first main sensor M1, the second detection information transmitted by the second main sensor M2, and the third detection information transmitted by the hub sensor H1.

The memory 22 is a storage device capable of storing various types of information, such as a random access memory (RAM), a hard disk drive (HDD), a solid state drive (SSD), or a flash memory. The memory 22 includes a detection information storage 221, a distance table storage 222, and a travel distance storage 223.

The detection information storage 221 stores the first detection information transmitted by the first main sensor M1, the second detection information transmitted by the second main sensor M2, and the third detection information transmitted by the hub sensor H1.

The distance table storage 222 stores a distance table in which a first combination of an installation location of the first main sensor M1 and an installation location of the hub sensor H1 is associated with a first distance between the first main sensor M1 and the hub sensor H1, and a second combination of an installation location of the second main sensor M2 and an installation location of the hub sensor H1 is associated with a second distance between the second main sensor M2 and the hub sensor H1.

The travel distance storage 223 stores a travel distance of a resident of the house 100. The travel distance storage 223 may store a travel distance for each house 100 or may store a travel distance for each resident.

The processor 21 is a central processing unit (CPU), for example. The processor 21 serves as a detection information acquisition unit 211, a travel distance calculation unit 212, and a travel distance output unit 213.

The detection information acquisition unit 211 acquires the first detection information indicating that a person is detected by the first main sensor M1 provided in the first space 101 in the house 100, the second detection information indicating that the person is detected by the second main sensor M2 provided in the second space 102 different from the first space 101 in the house 100, and the third detection information indicating that the person is detected by the hub sensor H1 provided in the third space 103 connecting the first space 101 and the second space 102 in the house 100. The detection information acquisition unit 211 reads out the first detection information, the second detection information, and the third detection information stored in the detection information storage 221.

The travel distance calculation unit 212 arranges the first detection information, the second detection information, and the third detection information output from the respective sensors in a predetermined period in chronological order. The predetermined period is one day, for example.

The travel distance calculation unit 212 adds the first distance between the first main sensor M1 and the hub sensor H1 to the travel distance based on the first detection information and the third detection information when the person is detected by the hub sensor H1 after the person is detected by the first main sensor M1 or when the person is detected by the first main sensor M1 after the person is detected by the hub sensor H1.

The travel distance calculation unit 212 also adds the second distance between the second main sensor M2 and the hub sensor H1 to the travel distance based on the second detection information and the third detection information when the person is detected by the hub sensor H1 after the person is detected by the second main sensor M2 or when the person is detected by the second main sensor M2 after the person is detected by the hub sensor H1.

The travel distance calculation unit 212 adds no third distance between the first main sensor M1 and the second main sensor M2 to the travel distance based on the first detection information and the second detection information when the person is detected by the second main sensor M2 after the person is detected by the first main sensor M1 or when the person is detected by the first main sensor M1 after the person is detected by the second main sensor M2.

That is, when the person is detected by the hub sensor H1 after the person is detected by the first main sensor M1, it is estimated that the person has moved from the first space 101 to the third space 103, and then the first distance between the first main sensor M1 and the hub sensor H1 is added to the travel distance. In contrast, when the person is detected by the second main sensor M2 after the person is detected by the first main sensor M1, the person has not passed through the third space 103 through which the person should pass when traveling from the first space 101 to the second space 102. Thus, it is estimated that the second main sensor M2 has erroneously detected the person, so that the third distance between the first main sensor M1 and the second main sensor M2 is not added to the travel distance.

The travel distance calculation unit 212 reads out the first distance associated with the first combination of the installation location of the first main sensor M1 and the installation location of the hub sensor H1 from the distance table stored in the distance table storage 222 and adds the first distance to the travel distance when the person is detected by the hub sensor H1 after the person is detected by the first main sensor M1, or when the person is detected by the first main sensor M1 after the person is detected by the hub sensor H1.

The travel distance calculation unit 212 reads out the second distance associated with the second combination of the installation location of the second main sensor M2 and the installation location of the hub sensor H1 from the distance table stored in the distance table storage 222 and adds the second distance to the travel distance when the person is detected by the hub sensor H1 after the person is detected by the second main sensor M2, or when the person is detected by the second main sensor M2 after the person is detected by the hub sensor H1.

When the person is detected by the first main sensor M1 after the person is detected by the first main sensor M1, the travel distance calculation unit 212 does not add a distance between the first main sensor M1 at the first detection and the first main sensor M1 at the second detection to the travel distance. This is because it is estimated that the person has not traveled from the first space 101 when the person is detected by the first main sensor M1 after the person is detected by the first main sensor M1. Similarly, when the person is detected by the second main sensor M2 after the person is detected by the second main sensor M2, the travel distance calculation unit 212 does not add a distance between the second main sensor M2 at the first detection and the second main sensor M2 at the second detection to the travel distance. When the person is detected by the hub sensor H1 after the person is detected by the hub sensor H1, the travel distance calculation unit 212 does not add a distance between the hub sensor H1 at the first detection and the hub sensor H1 at the second detection to the travel distance.

The distance table is configured such that a third combination of the installation location of the first main sensor M1 and the installation location of the second main sensor M2 is not associated with the third distance between the first main sensor M1 and the second main sensor M2. Thus, when the person is detected by the second main sensor M2 after the person is detected by the first main sensor M1, or when the person is detected by the first main sensor M1 after the person is detected by the second main sensor M2, the third distance associated with the third combination of the installation location of the first main sensor M1 and the installation location of the second main sensor M2 is not in the distance table, and thus the third distance between the first main sensor M1 and the second main sensor M2 is not added to the travel distance.

The distance table may be configured such that the third combination of the installation location of the first main sensor M1 and the installation location of the second main sensor M2 is associated with 0 meter. As a result, when the person is detected by the second main sensor M2 after the person is detected by the first main sensor M1, or when the person is detected by the first main sensor M1 after the person is detected by the second main sensor M2, 0 meter is added to the travel distance, and thus the third distance between the first main sensor M1 and the second main sensor M2 is not added to the travel distance.

The travel distance output unit 213 outputs the travel distance added by the travel distance calculation unit 212. The travel distance output unit 213 may output the travel distance of the person in the predetermined period to the memory 22 to store the travel distance in the travel distance storage 223. The travel distance output unit 213 may output the travel distance of the person in the predetermined period to the communication unit 23. In this case, the communication unit 23 may transmit the travel distance of the person in the predetermined period to an information terminal (not illustrated). The information terminal is a smartphone, a tablet computer, or a personal computer, for example. The information terminal is used by the resident of the house 100, a caregiver of the resident of the house 100, or a care manager of the resident of the house 100, for example.

Figure 2:
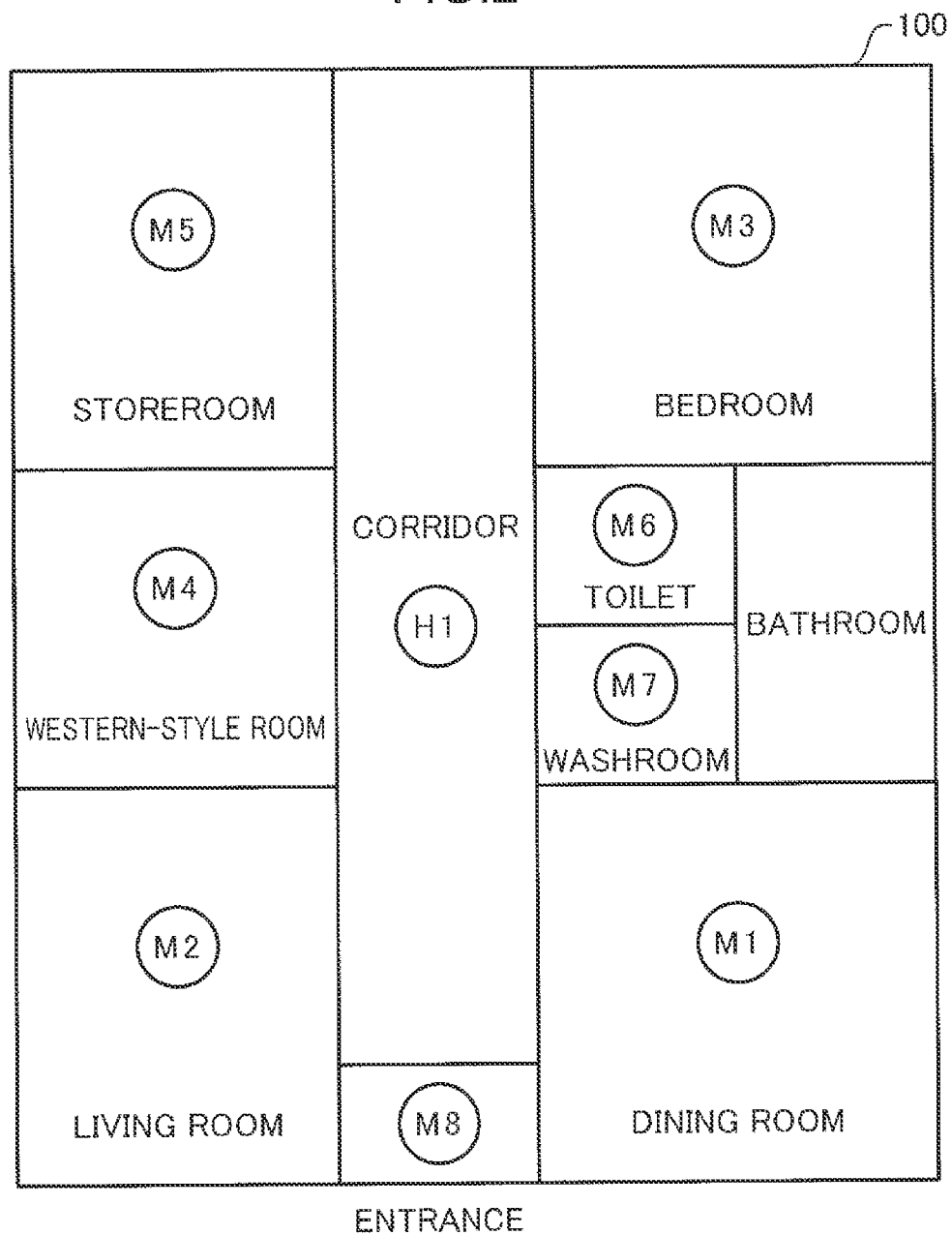
FIG. 2 is a diagram illustrating an example of a room layout of a house in which a main sensor and a hub sensor are installed in the first embodiment.

FIG. 2 is a diagram illustrating an example of a room layout of the house in which the main sensor and the hub sensor are installed in the first embodiment.

As illustrated in FIG. 2, first to eighth main sensors M1 to M8 and the hub sensor H1 are installed one by one in respective rooms in the house 100. The first to eighth main sensors M1 to M8 are installed in the dining room, the living room, the bedroom, a western-style room, a storeroom, the toilet, the washroom, and an entrance, respectively, and the hub sensor H1 is installed in the corridor. When the person travels from a room in which the main sensor is installed to another room in which another main sensor is installed, the person needs to pass through the corridor in which the hub sensor H1 is installed.

FIG. 3 is a diagram illustrating an example of the distance table stored in the distance table storage 222 in the first embodiment.

As illustrated in FIG. 3, a distance is associated with a combination of the corridor in which the hub sensor H1 is installed and the corresponding one of the rooms in which the respective first to eighth main sensors M1 to M8 are installed. For example, a combination of the corridor and the dining room is associated with the first distance of 4 meters between the first main sensor M1 and the hub sensor H1. For example, when the person travels from the dining room to the corridor, 4 meters are added to the travel distance.

The first detection information may include information indicating the installation location (dining room) of the first main sensor M1, the second detection information may include information indicating the installation location (living room) of the second main sensor M2, and the third detection information may include information indicating the installation location (corridor) of the hub sensor H1. As a result, the installation location can be specified from the detection information.

The first detection information may include identification information for identifying the first main sensor M1, the second detection information may include identification information for identifying the second main sensor M2, and the third detection information may include identification information for identifying the hub sensor H1. In this case, the memory 22 may store a table in which the identification information on each of the sensors is associated with the installation location of the corresponding one of the sensors. As a result, the installation location can be specified from the detection information.

Figure 4:
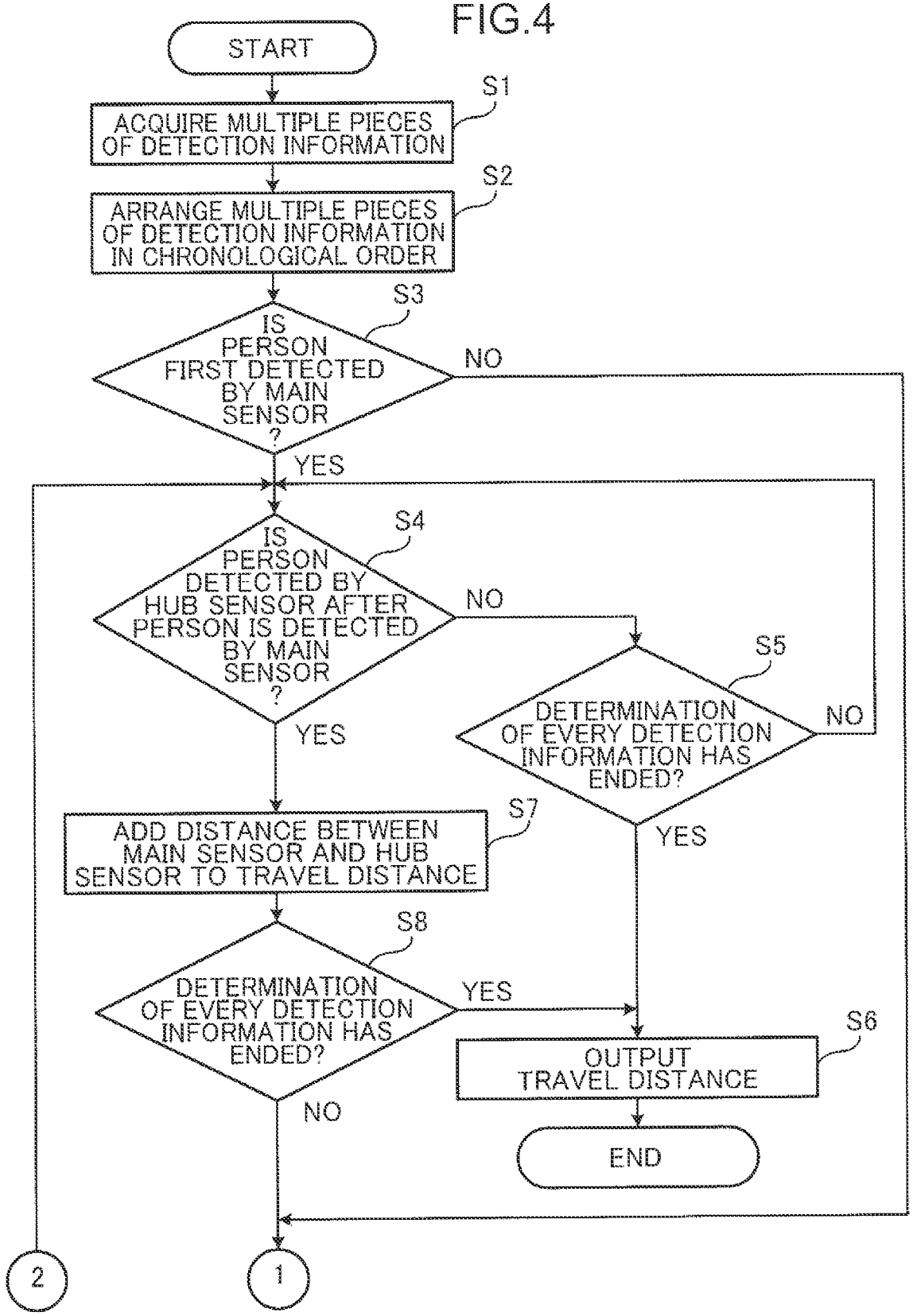
FIG. 4 is a first flowchart for illustrating travel distance calculation processing in a travel distance calculation device according to the first embodiment of the present disclosure.
Figure 5:
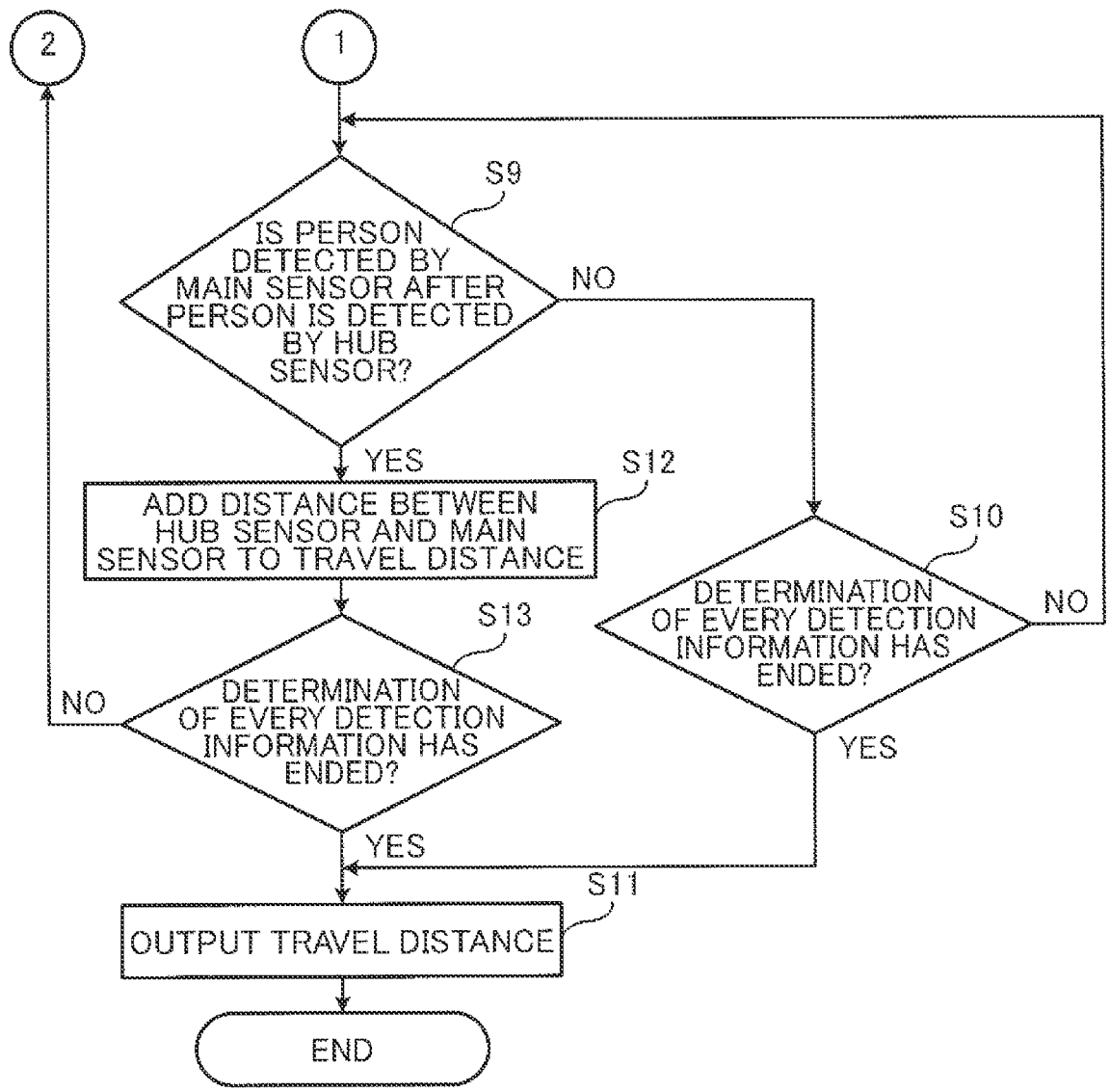
FIG. 5 is a second flowchart for illustrating travel distance calculation processing in the travel distance calculation device according to the first embodiment of the present disclosure.

FIG. 4 is a first flowchart for illustrating travel distance calculation processing in the travel distance calculation device 2 according to the first embodiment of the present disclosure, and FIG. 5 is a second flowchart for illustrating the travel distance calculation processing in the travel distance calculation device 2 according to the first embodiment of the present disclosure. In the following description, a main sensor MN is a general term for the first to eighth main sensors M1 to M8.

First, the detection information acquisition unit 211 acquires multiple pieces of detection information output by the main sensor MN and the hub sensor H1 from the detection information storage 221 in step S1.

For example, the travel distance calculation processing illustrated in FIGS. 4 and 5 is performed once a day. The detection information acquisition unit 211 acquires detection information for one day at 0:00 AM, for example. Time at which the detection information is acquired is not limited to 0:00 AM. The travel distance calculation processing illustrated in FIGS. 4 and 5 is not limited to being performed once a day, and may be performed multiple times a day, once a week, or every predetermined period.

Next, the travel distance calculation unit 212 arranges the multiple pieces of detection information acquired by the detection information acquisition unit 211 in chronological order in step S2.

Subsequently, the travel distance calculation unit 212 determines whether a person is first detected by the main sensor MN in step S3 based on the detection information arranged in chronological order. Here, when it is determined that the person is not detected by the main sensor MN first, in other words, when the person is first detected by the hub sensor H1 (NO in step S3), processing proceeds to step S9.

In contrast, when it is determined that the person is first detected by the main sensor MN (YES in step S3), the travel distance calculation unit 212 determines whether the person is detected by the hub sensor H1 after the person is detected by the main sensor MN based on the detection information arranged in chronological order, in step S4.

Here, when it is determined that the person is not detected by the hub sensor H1 after the person is detected by the main sensor MN, in other words, when it is determined that the person is detected by the main sensor MN after the person is detected by the main sensor MN (NO in step S4), the travel distance calculation unit 212 determines whether determination of every detection information acquired is ended, in step S5. Then, when it is determined that the determination of every detection information acquired is ended (YES in step S5), the travel distance output unit 213 outputs the travel distance added by the travel distance calculation unit 212, in step S6. For example, the travel distance output unit 213 outputs the travel distance to the travel distance storage 223. The travel distance storage 223 stores the travel distance output by the travel distance output unit 213.

In contrast, when it is determined that the determination of every detection information acquired is not ended (NO in step S5), the processing returns to step S4. As described above, when the person is detected continuously by the same main sensor MN, it is estimated that the person has not traveled from a room in which the main sensor MN is installed. Thus, a distance between two main sensors is not added to the travel distance. When the person is detected continuously by the main sensors MN different from each other, it is estimated that the subsequent main sensor MN has erroneously detected the person. Thus, a distance between the two main sensors is not added to the travel distance.

When it is determined that the person is detected by the hub sensor H1 after the person is detected by the main sensor MN (YES in step S4), the travel distance calculation unit 212 adds a distance between the main sensor MN and the hub sensor H1 to the travel distance in step S7. At this time, the travel distance calculation unit 212 reads out a distance associated with a combination of an installation location of the main sensor MN and an installation location of the hub sensor H1 from the distance table stored in the distance table storage 222, and adds the distance to the travel distance.

Next, the travel distance calculation unit 212 determines whether the determination of every detection information acquired is ended, in step S8. Here, when it is determined that the determination of every detection information acquired is ended (YES in step S8), the processing proceeds to step S6.

In contrast, when it is determined that the determination of every detection information acquired is not ended (NO in step S8), the travel distance calculation unit 212 determines whether the person is detected by the main sensor MN after the person is detected by the hub sensor H1, in step S9, based on the detection information arranged in chronological order.

When it is determined that the person is not detected by the main sensor MN after the person is detected by the hub sensor H1, in other words, when it is determined that the person is detected by the hub sensor H1 after the person is detected by the hub sensor H1 (NO in step S9), the travel distance calculation unit 212 determines whether the determination of every detection information acquired is ended, in step S10. Then, when it is determined that the determination of every detection information acquired is ended (YES in step S10), the travel distance output unit 213 outputs the travel distance added by the travel distance calculation unit 212, in step S11. For example, the travel distance output unit 213 outputs the travel distance to the travel distance storage 223. The travel distance storage 223 stores the travel distance output by the travel distance output unit 213.

In contrast, when it is determined that the determination of every detection information acquired is not ended (NO in step S10), the processing returns to step S9. As described above, when the person is detected continuously by the same hub sensor H1, it is estimated that the person has not traveled from a room in which the hub sensor H1 is installed. Thus, a distance between two hub sensors is not added to the travel distance.

When it is determined that the person is detected by the main sensor MN after the person is detected by the hub sensor H1 (YES in step S9), the travel distance calculation unit 212 adds the distance between the main sensor MN and the hub sensor H1 to the travel distance in step S12. At this time, the travel distance calculation unit 212 reads out a distance associated with the combination of the installation location of the hub sensor H1 and the installation location of the main sensor MN from the distance table stored in the distance table storage 222, and adds the distance to the travel distance.

Next, the travel distance calculation unit 212 determines whether the determination of every detection information acquired is ended, in step S13. Here, when it is determined that the determination of every detection information acquired is ended (YES in step S13), the processing proceeds to step S11.

In contrast, when it is determined that the determination of every detection information acquired is not ended (NO in step S13), the processing returns to step S4.

Figure 6:
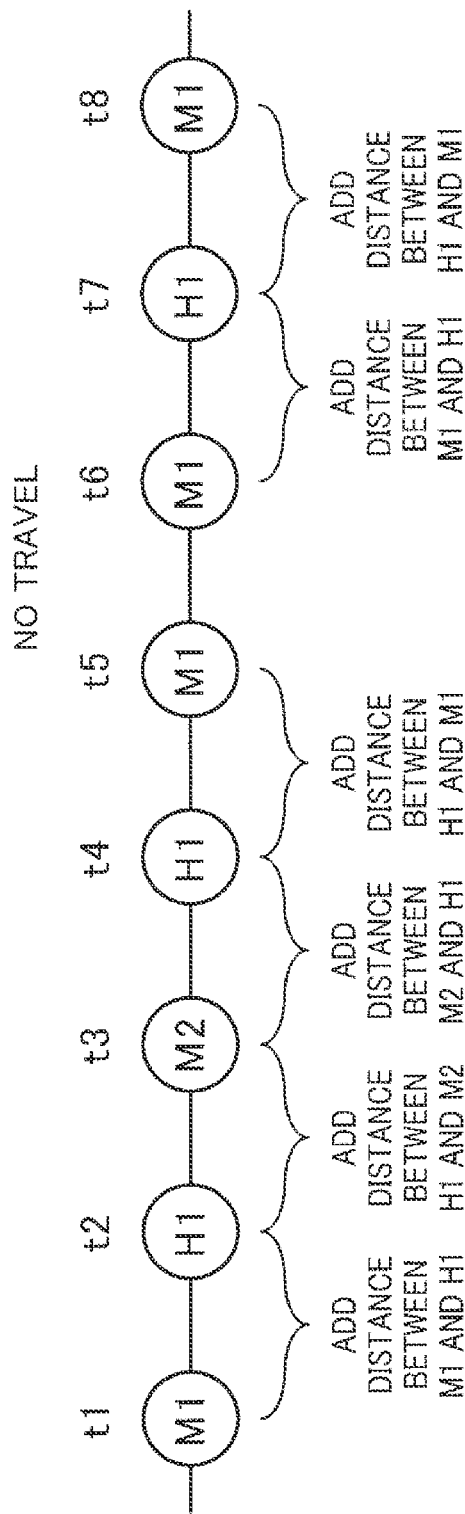
FIG. 6 is a diagram illustrating the main sensor and the hub sensor that output detection information and that are arranged in chronological order when the main sensor and the hub sensor normally detect a person in the first embodiment.

FIG. 6 is a diagram illustrating the main sensor and the hub sensor that output detection information and that are arranged in chronological order when the main sensor and the hub sensor normally detect the person in the first embodiment.

The hub sensor H1 detects the person at time t2 after the first main sensor M1 detects the person at time t1, so that the first distance between the first main sensor M1 and the hub sensor H1 is added to the travel distance. Then, the second main sensor M2 detects the person at time t3 after the hub sensor H1 detects the person at time 12, so that the second distance between the second main sensor M2 and the hub sensor H1 is added to the travel distance. Then, the hub sensor H1 detects the person at time t4 after the second main sensor M2 detects the person at time t3, so that the second distance between the second main sensor M2 and the hub sensor H1 is added to the travel distance.

The first main sensor M1 detects the person at time t5 after the hub sensor H1 detects the person at time t4, so that the first distance between the first main sensor M1 and the hub sensor H1 is added to the travel distance. Then, the first main sensor M1 detects the person at time t6 after the first main sensor M1 detects the person at time t5, so that the distance between the first main sensor M1 at the former detection and the first main sensor M1 at the latter detection is not added to the travel distance. This is because it is estimated that the person has not traveled from the first space 101.

The hub sensor H1 detects the person at time t7 after the first main sensor M1 detects the person at time t6, so that the first distance between the first main sensor M1 and the hub sensor H1 is added to the travel distance. Then, the first main sensor M1 detects the person at time t8 after the hub sensor H1 detects the person at time t7, so that the first distance between the first main sensor M1 and the hub sensor H1 is added to the travel distance.

Figure 7:
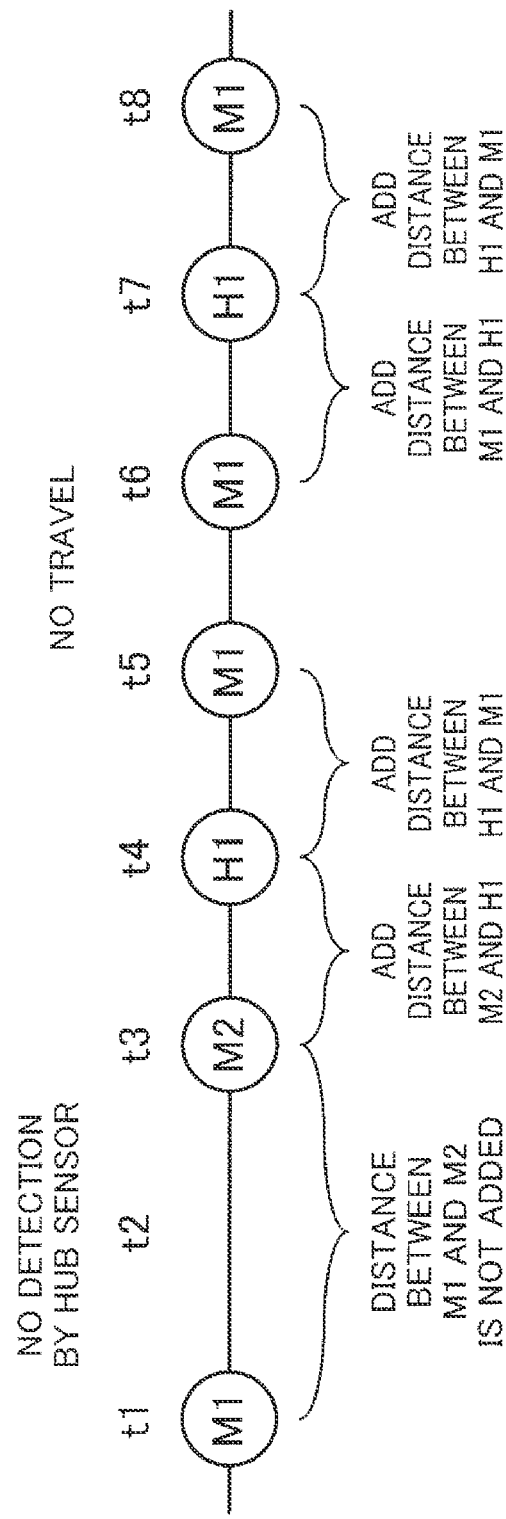
FIG. 7 is a diagram illustrating the main sensor and the hub sensor that output detection information and that are arranged in chronological order when the hub sensor does not normally detect the person in the first embodiment.

FIG. 7 is a diagram illustrating the main sensor and the hub sensor that output detection information and that are arranged in chronological order when the hub sensor does not normally detect the person in the first embodiment.

FIG. 7 shows that the hub sensor H1 does not normally detect the person at time t2, and the second main sensor M2 detects the person at time 3 after the first main sensor M1 detects the person at time t1. In this case, the person is detected by the second main sensor M2 after the person is detected by the first main sensor M1, so that the third distance between the first main sensor M1 and the second main sensor M2 is not added to the travel distance.

Figure 8:
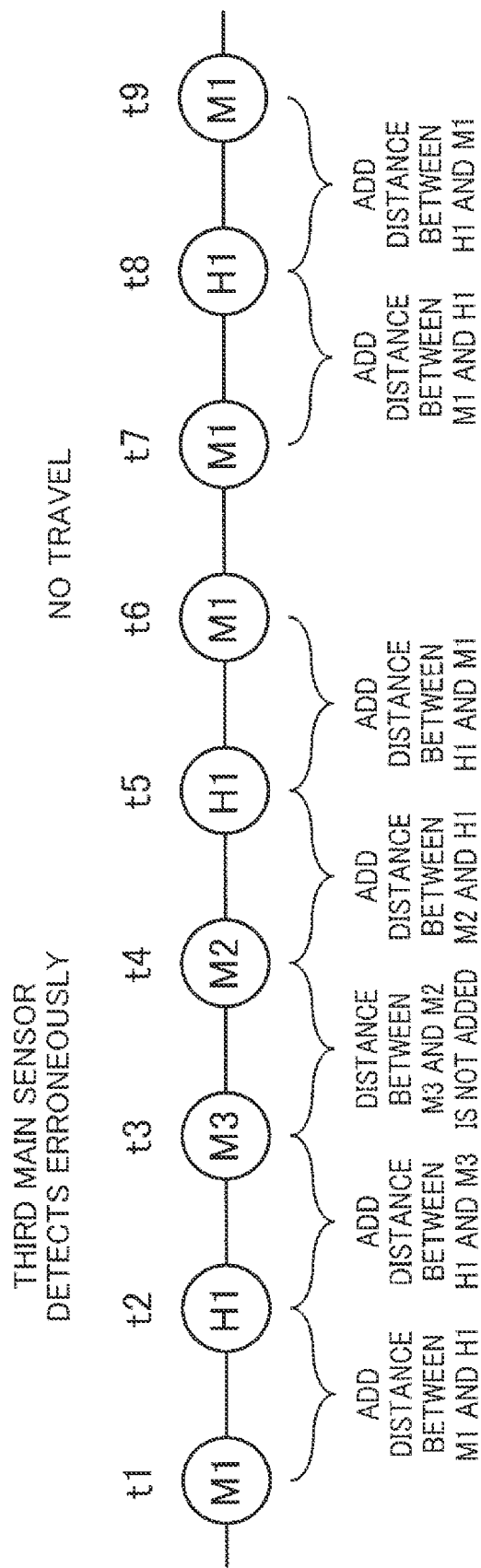
FIG. 8 is a diagram illustrating the main sensor and the hub sensor that output detection information and that are arranged in chronological order when the main sensor erroneously detects the person in the first embodiment.

FIG. 8 is a diagram illustrating the main sensor and the hub sensor that output detection information and that are arranged in chronological order when the main sensor erroneously detects the person in the first embodiment.

FIG. 8 shows that a third main sensor M3 erroneously detects the person at time t3. Thus, the third main sensor M3 detects the person at time t3 after the hub sensor H1 detects the person at time 2. In this case, the person is detected by the third main sensor M3 after the person is detected by the hub sensor H1, so that a distance between the hub sensor H1 and the third main sensor M3 is added to the travel distance. Then, the second main sensor M2 detects the person at time t4 after the third main sensor M3 detects the person at time t3. In this case, the person is detected by the second main sensor M2 after the person is detected by the third main sensor M3, so that a distance between the second main sensor M3 and the third main sensor M2 is not added to the travel distance.

As described above, when the first main sensor M1 provided in the first space 101 detects the person and then the second main sensor M2 provided in the second space 102 detects the person, for example, the third distance between the first main sensor M1 and the second main sensor M2 is not added to the travel distance because the person has not passed through the third space 103 and a flow line of the person is not correctly captured. Thus, the distance between the sensors is added to the travel distance in consideration of the flow line of the person, so that the travel distance of the person can be calculated even when the sensors react erroneously.

The first space 101, the second space 102, and the third space 103 are respectively provided with the first main sensor M1, the second main sensor M2, and the hub sensor H1 one by one, so that multiple sensors are not required for each space, and thus enabling reduction in cost for installing the multiple sensors.

The travel distance calculation unit 212 in the first embodiment may not calculate the travel distance when any two of the first main sensor M1, the second main sensor M2, and the hub sensor H1 simultaneously detect the person. For example, when a caregiver visits a house of a care receiver while the travel distance calculation device 2 calculates a travel distance of a resident who is the care receiver, the main sensor and the hub sensor detect not only the care receiver but also the caregiver, and thus an accurate travel distance of the care receiver cannot be calculated. Thus, when any two of the multiple main sensors and the hub sensor simultaneously detect the person, the travel distance calculation unit 212 may estimate that multiple persons are in the house and stop calculating the travel distance. This configuration causes no travel distance to be calculated when a person other than a subject (resident) for which a travel distance is to be calculated is in the house, and thus enabling calculation of the travel distance of only the subject.

Second Embodiment

The house 100 in the first embodiment described above is provided with a main sensor or a hub sensor one by one in each space. In contrast, a second embodiment includes at least one sub-sensor provided in addition to the main sensor or the hub sensor provided in each space.

Figure 9:
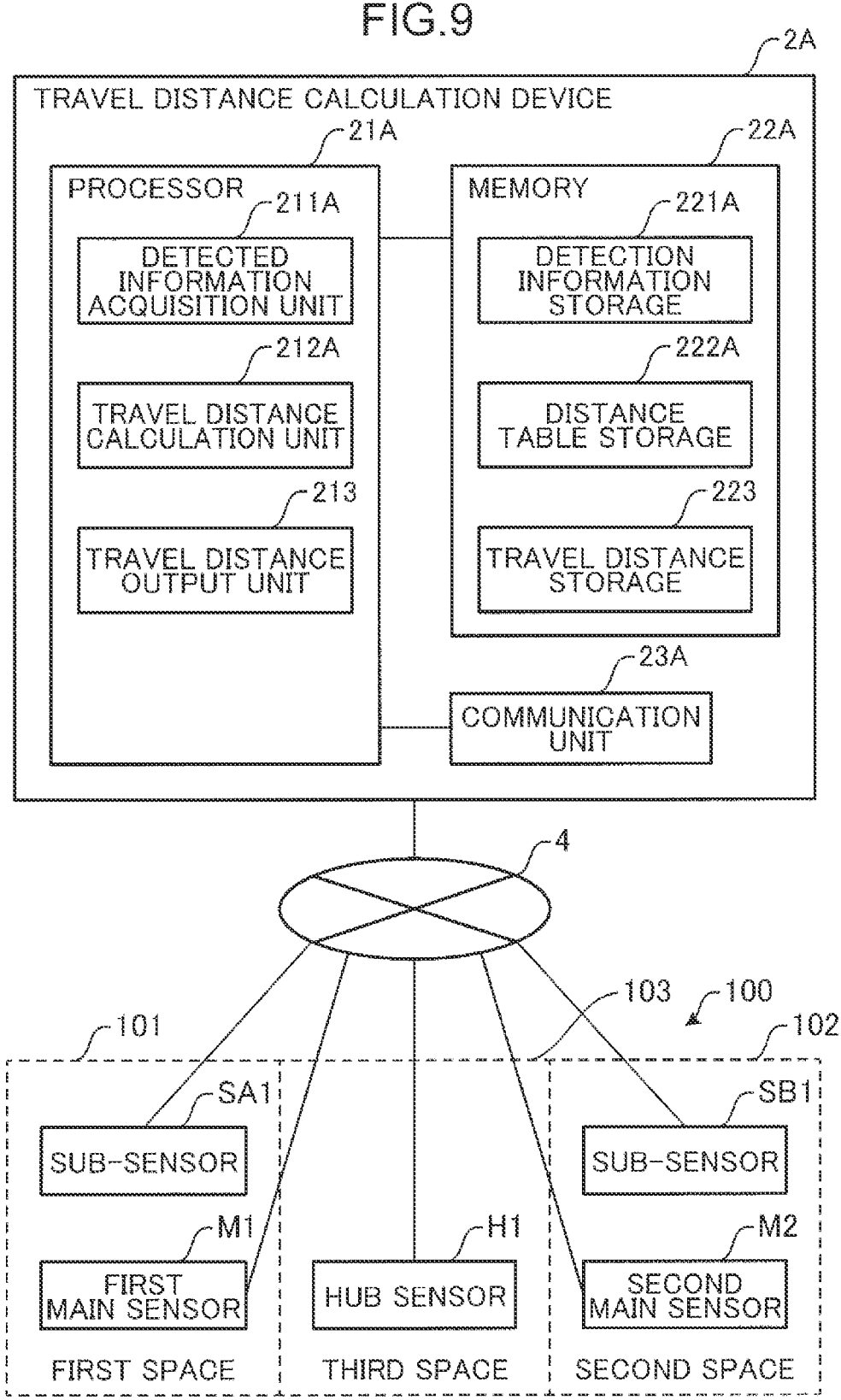
FIG. 9 is a block diagram illustrating a configuration of a travel distance calculation system according to a second embodiment of the present disclosure.

FIG. 9 is a block diagram illustrating a configuration of a travel distance calculation system according to the second embodiment of the present disclosure.

The travel distance calculation system illustrated in FIG. 9 includes a first main sensor M1, a second main sensor M2, a hub sensor H1, sub-sensors SA1 and SB1, and a travel distance calculation device 2A. In the second embodiment, the same components as those in the first embodiment are denoted by the same reference numerals, and duplicated description thereof will be omitted.

The first main sensor M1 is provided at a first position in a first space 101 in a house 100 to detect a person at the first position in the first space 101. The first position is an entrance of the first space 101, for example. When detecting the person at the first position in the first space 101, the first main sensor M1 transmits first detection information indicating that the person is detected to the travel distance calculation device 2A. The first detection information includes time information indicating time at which the person is detected.

The sub-sensor SA1 is provided at a second position different from the first position where the first main sensor M1 is provided in the first space 101 to detect the person at the second position. The sub-sensor SA1 is a motion sensor or an opening-closing sensor of a door of an electric device provided at the second position in the first space 101, for example. When detecting the person at the second position in the first space 101, the sub-sensor SA1 transmits fourth detection information indicating that the person is detected to the travel distance calculation device 2A. The fourth detection information includes time information indicating time at which the person is detected.

The second main sensor M2 is provided at a first position in a second space 102 different from the first space 101 in the house 100 to detect the person at the first position in the second space 102. The first position is an entrance of the second space 102, for example. When detecting the person at the first position in the second space 102, the second main sensor M2 transmits second detection information indicating that the person is detected to the travel distance calculation device 2A. The second detection information includes time information indicating time at which the person is detected.

The sub-sensor SB1 is provided at a second position different from the first position where the second main sensor M2 is provided in the second space 102 to detect the person at the second position. The sub-sensor SB1 is a motion sensor or an opening-closing sensor of a door of an electric device provided at the second position in the second space 102, for example. When detecting the person at the second position in the second space 102, the sub-sensor SB1 transmits the fourth detection information indicating that the person is detected to the travel distance calculation device 2A. The fourth detection information includes time information indicating time at which the person is detected.

The sub-sensors SA1 and SB1 are each an example of the fourth sensor. The number of sub-sensors installed in one space is not limited to one, and multiple sub-sensors may be installed in one space.

The travel distance calculation device 2A is communicably connected to each of the first main sensor M1, the second main sensor M2, the hub sensor H1, and the sub-sensors SA1 and SB1 via a network 4.

The travel distance calculation device 2A includes a processor 21A, a memory 22A, and a communication unit 23A.

The communication unit 23A receives the first detection information transmitted by the first main sensor M1, the second detection information transmitted by the second main sensor M2, the third detection information transmitted by the hub sensor H1, and the fourth detection information transmitted by the sub-sensors SA1 and SB1.

The memory 22A is a storage device capable of storing various types of information, such as a RAM, an HDD, an SSD, or a flash memory. The memory 22A includes a detection information storage 221A, a distance table storage 222A, and a travel distance storage 223.

The detection information storage 221A stores the first detection information transmitted by the first main sensor M1, the second detection information transmitted by the second main sensor M2, the third detection information transmitted by the hub sensor H1, and the fourth detection information transmitted by the sub-sensors SA1 and SB1.

The distance table storage 222A stores a distance table in which a first combination of an installation location of the first main sensor M1 and an installation location of the hub sensor H1 is associated with a first distance between the first main sensor M1 and the hub sensor H1, and a second combination of an installation location of the second main sensor M2 and an installation location of the hub sensor H1 is associated with a second distance between the second main sensor M2 and the hub sensor H1.

The distance table is configured such that a combination of the installation location of the first main sensor M1 and an installation location of the sub-sensor SA1 is associated with a distance between the first main sensor M1 and the sub-sensor SA1. When multiple sub-sensors are installed in the first space 101, the distance table may be configured such that a combination of the installation location of the first main sensor M1 and the installation location of each of the sub-sensors is associated with a distance between the first main sensor M1 and the corresponding one of the sub-sensors, and a combination of the installation locations of the two sub-sensors is associated with a distance between the two sub-sensors.

The distance table is also configured such that a combination of the installation location of the second main sensor M2 and an installation location of the sub-sensor SB1 is associated with a distance between the second main sensor M2 and the sub-sensor SB1. When multiple sub-sensors are installed in the second space 102, the distance table may be configured such that a combination of the installation location of the second main sensor M2 and the installation location of each of the sub-sensors is associated with a distance between the second main sensor M2 and the corresponding one of the sub-sensors, and a combination of the installation locations of the two sub-sensors is associated with a distance between the two sub-sensors.

The processor 21A is a CPU, for example. The processor 21A serves as a detection information acquisition unit 211A, a travel distance calculation unit 212A, and a travel distance output unit 213.

The detection information acquisition unit 211A acquires first detection information indicating that the person is detected by the first main sensor M1, second detection information indicating that the person is detected by the second main sensor M2, and third detection information indicating that the person is detected by the hub sensor H1 provided in a third space 103. The detection information acquisition unit 211A reads out the first detection information, the second detection information, and the third detection information stored in the detection information storage 221A.

The detection information acquisition unit 211A further acquires fourth detection information indicating that the person is detected by the sub-sensor SA1 provided at a position different from the position where the first main sensor M1 is provided in the first space 101. The detection information acquisition unit 211A reads out the fourth detection information stored in the detection information storage 221A.

The travel distance calculation unit 212A arranges the first detection information, the second detection information, the third detection information, and the fourth detection information output from the respective sensors in a predetermined period in chronological order. The predetermined period is one day, for example.

The travel distance calculation unit 212A adds the first distance between the first main sensor M1 and the hub sensor H1 to the travel distance based on the first detection information and the third detection information when the person is detected by the hub sensor H1 after the person is detected by the first main sensor M1 or when the person is detected by the first main sensor M1 after the person is detected by the hub sensor H1.

The travel distance calculation unit 212A also adds the second distance between the second main sensor M2 and the hub sensor H1 to the travel distance based on the second detection information and the third detection information when the person is detected by the hub sensor H1 after the person is detected by the second main sensor M2 or when the person is detected by the second main sensor M2 after the person is detected by the hub sensor H1.

The travel distance calculation unit 212A adds no third distance between the first main sensor M1 and the second main sensor M2 to the travel distance based on the first detection information and the second detection information when the person is detected by the second main sensor M2 after the person is detected by the first main sensor M1 or when the person is detected by the first main sensor M1 after the person is detected by the second main sensor M2.

The travel distance calculation unit 212A adds the distance between the first main sensor M1 and the sub-sensor SA1 to the travel distance based on the first detection information and the fourth detection information when the person is detected by the sub-sensor SA1 in the first space 101 after the person is detected by the first main sensor M1 or when the person is detected by the first main sensor M1 after the person is detected by the sub-sensor SA1 in the first space 101.

The travel distance calculation unit 212A also adds the distance between the second main sensor M2 and the sub-sensor SB1 to the travel distance based on the second detection information and the fourth detection information when the person is detected by the sub-sensor SB1 in the second space 102 after the person is detected by the second main sensor M2 or when the person is detected by the second main sensor M2 after the person is detected by the sub-sensor SB1 in the second space 102.

The travel distance calculation unit 212A does not add a distance between the first main sensor M1 and the sub-sensor SB1 to the travel distance based on the first detection information and the fourth detection information when the person is detected by the sub-sensor SB1 in the second space 102 after the person is detected by the first main sensor M1 or when the person is detected by the first main sensor M1 after the person is detected by the sub-sensor SB1 in the second space 102.

The travel distance calculation unit 212A also does not add a distance between the second main sensor M2 and the sub-sensor SA1 to the travel distance based on the second detection information and the fourth detection information when the person is detected by the sub-sensor SA1 in the first space 101 after the person is detected by the second main sensor M2 or when the person is detected by the second main sensor M2 after the person is detected by the sub-sensor SA1 in the first space 101.

The travel distance calculation unit 212A reads out a distance associated with the combination of the installation location of the first main sensor M1 and the installation location of the sub-sensor SA1 from the distance table stored in the distance table storage 222A and adds the distance to the travel distance when the person is detected by the sub-sensor SA1 in the first space 101 after the person is detected by the first main sensor M1, or when the person is detected by the first main sensor M1 after the person is detected by the sub-sensor SA1 in the first space 101.

The travel distance calculation unit 212A also reads out a distance associated with the combination of the installation location of the second main sensor M2 and the installation location of the sub-sensor SB1 from the distance table stored in the distance table storage 222A and adds the distance to the travel distance when the person is detected by the sub-sensor SB1 in the second space 102 after the person is detected by the second main sensor M2, or when the person is detected by the second main sensor M2 after the person is detected by the sub-sensor SB1 in the second space 102.

The travel distance calculation unit 212A adds the first distance between the first main sensor M1 and the hub sensor H1 to the travel distance without adding the second distance between the second main sensor M2 and the hub sensor H1 to the travel distance when the person is detected by the second main sensor M2 after the person is detected by the hub sensor H1, and the person is detected continuously three or more times by at least one of the first main sensor M1 and the sub-sensor SA1 in the first space 101 after the person is detected by the second main sensor M2.

That is, when the hub sensor H1, the second main sensor M2, and the first main sensor M1 sequentially detect the person, the hub sensor Il1 does not detect the person after the second main sensor M2 detects the person. Thus, any one of the second main sensor M2 and the first main sensor M1 may have erroneously detected the person. Here, when at least one of the first main sensor M1 and the sub-sensor SA1 in the first space 101 continuously detects the person three or more times after the second main sensor M2 detects the person, it can be estimated that the person has not traveled from the third space 103 to the second space 102 but has traveled from the third space 103 to the first space 101. Thus, the travel distance calculation unit 212A adds the first distance between the first main sensor M1 and the hub sensor Ill to the travel distance instead of adding the second distance between the second main sensor M2 and the hub sensor H1 to the travel distance.

Figure 10:
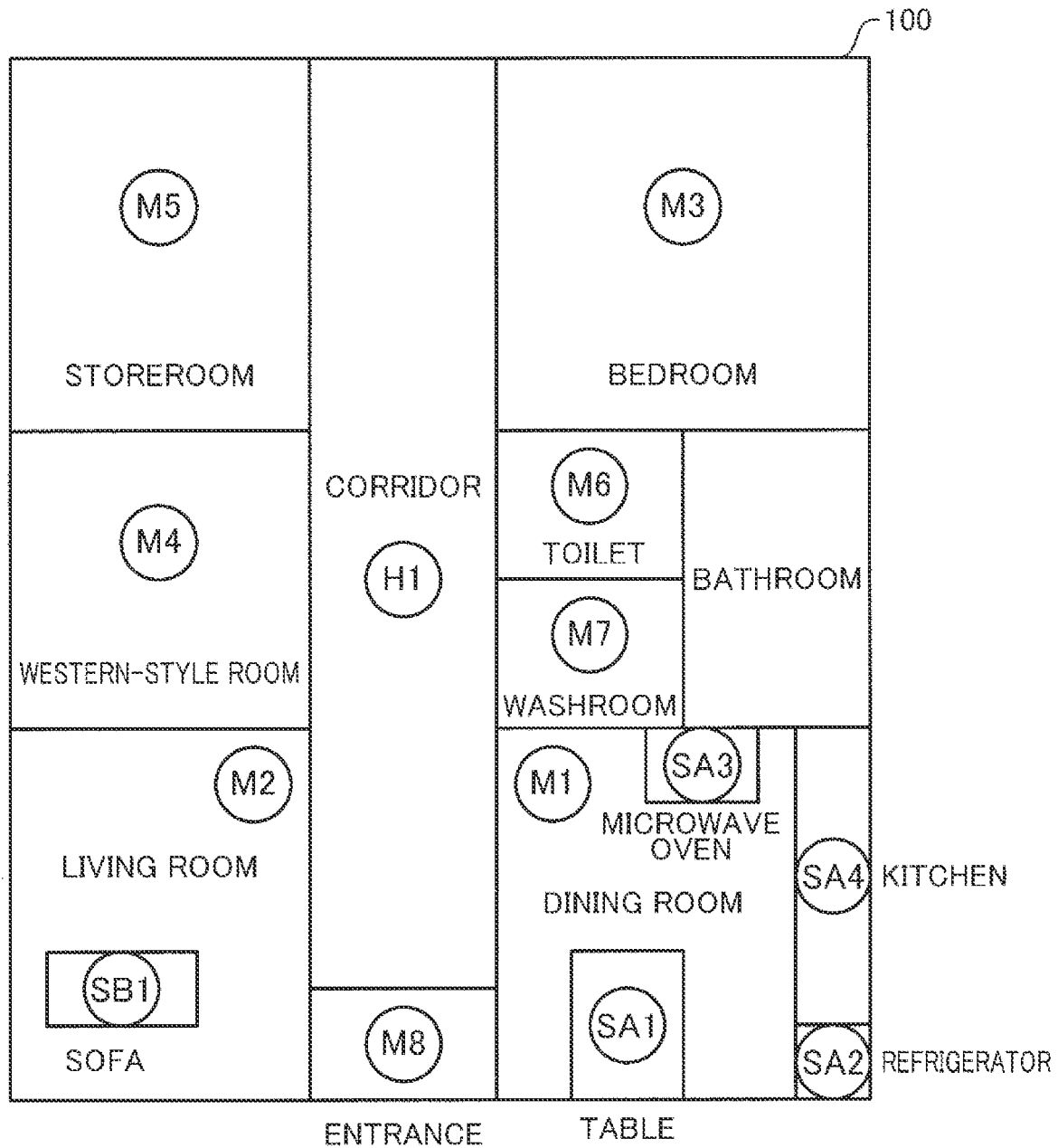
FIG. 10 is a diagram illustrating an example of a room layout of a house in which a main sensor, a hub sensor, and a sub-sensor are installed in the second embodiment.

FIG. 10 is a diagram illustrating an example of a room layout of the house in which the main sensor, the hub sensor, and the sub-sensor are installed in the second embodiment.

As illustrated in FIG. 10, the first to eighth main sensors M1 to M8 and the hub sensor H1 are installed one by one in respective rooms in the house 100. The first to eighth main sensors M1 to M8 are installed in the dining room, the living room, the bedroom, a western-style room, a storeroom, the toilet, the washroom, and an entrance, respectively, and the hub sensor H1 is installed in the corridor. In particular, the first main sensor M1 is installed at the entrance of the dining room, and the second main sensor M2 is installed at the entrance of the living room. When the person travels from a room in which the main sensor is installed to another room in which another main sensor is installed, the person needs to pass through the corridor in which the hub sensor H1 is installed.

The sub-sensors SA1 to SA4 are each installed in the dining room at a position different from the position where the first main sensor M1 is installed. Specifically, the sub-sensor SA1 is a motion sensor installed near a table to detect a person around the table. The sub-sensor SA2 is an opening-closing sensor installed on a door of a refrigerator to detect a person having opened or closed the door of the refrigerator. The sub-sensor SA3 is an opening-closing sensor installed on a door of a microwave oven to detect a person having opened or closed the door of the microwave oven. The sub-sensor SA4 is a motion sensor installed near a kitchen to detect a person in the kitchen.

The sub-sensor SB1 is installed the living room at a position different from the position where the second main sensor M2 is installed. Specifically, the sub-sensor SB1 is a motion sensor installed near a sofa to detect a person on the sofa.

FIG. 11 is a diagram illustrating an example of the distance table stored in the distance table storage 222A in the second embodiment.

As illustrated in FIG. 11, a distance is associated with a combination of the corridor in which the hub sensor H1 is installed and the corresponding one of the rooms in which the respective first to eighth main sensors M1 to M8 are installed. For example, a combination of the corridor and the dining room is associated with the first distance of 4 meters between the first main sensor M1 and the hub sensor H11. For example, when the person travels from the dining room to the corridor, 4 meters are added to the travel distance.

The first main sensor M1 is installed at the entrance of the dining room, and the second main sensor M2 is installed at the entrance of the living room. A distance is associated with a combination of the position where the first main sensor M1 is installed (the entrance of the dining room) and the position where the corresponding one of the sub-sensors SA1 to SA4 is installed (the table, the refrigerator, the microwave oven, or the kitchen). For example, a combination of the entrance of the dining room and the table is associated with a distance of 6 meters between the first main sensor M1 and the sub-sensor SA1. For example, when the person travels from the entrance of the dining room to the table, 6 meters are added to the travel distance.

Additionally, a distance is also associated with a combination of two sub-sensors. For example, a combination of the table and the refrigerator is associated with a distance of 2 meters between the sub-sensor SA1 and the sub-sensor SA2. For example, when the person travels from the table to the refrigerator in the dining room, 2 meters are added to the travel distance.

The first detection information may include information indicating the installation location (dining room) of the first main sensor M1, the second detection information may include information indicating the installation location (living room) of the second main sensor M2, the third detection information may include information indicating the installation location (corridor) of the hub sensor H1, and the fourth detection information may include information indicating the installation locations of the sub-sensors SA1 to SA4. As a result, the installation location can be specified from the detection information.

The first detection information may include identification information for identifying the first main sensor M1, the second detection information may include identification information for identifying the second main sensor M2, the third detection information may include identification information for identifying the hub sensor H1, and the fourth detection information may include identification information for identifying the sub-sensors SA1 to SA4. In this case, the memory 22 may store a table in which the identification information on each of the sensors is associated with the installation location of the corresponding one of the sensors. As a result, the installation location can be specified from the detection information.

Figure 14:
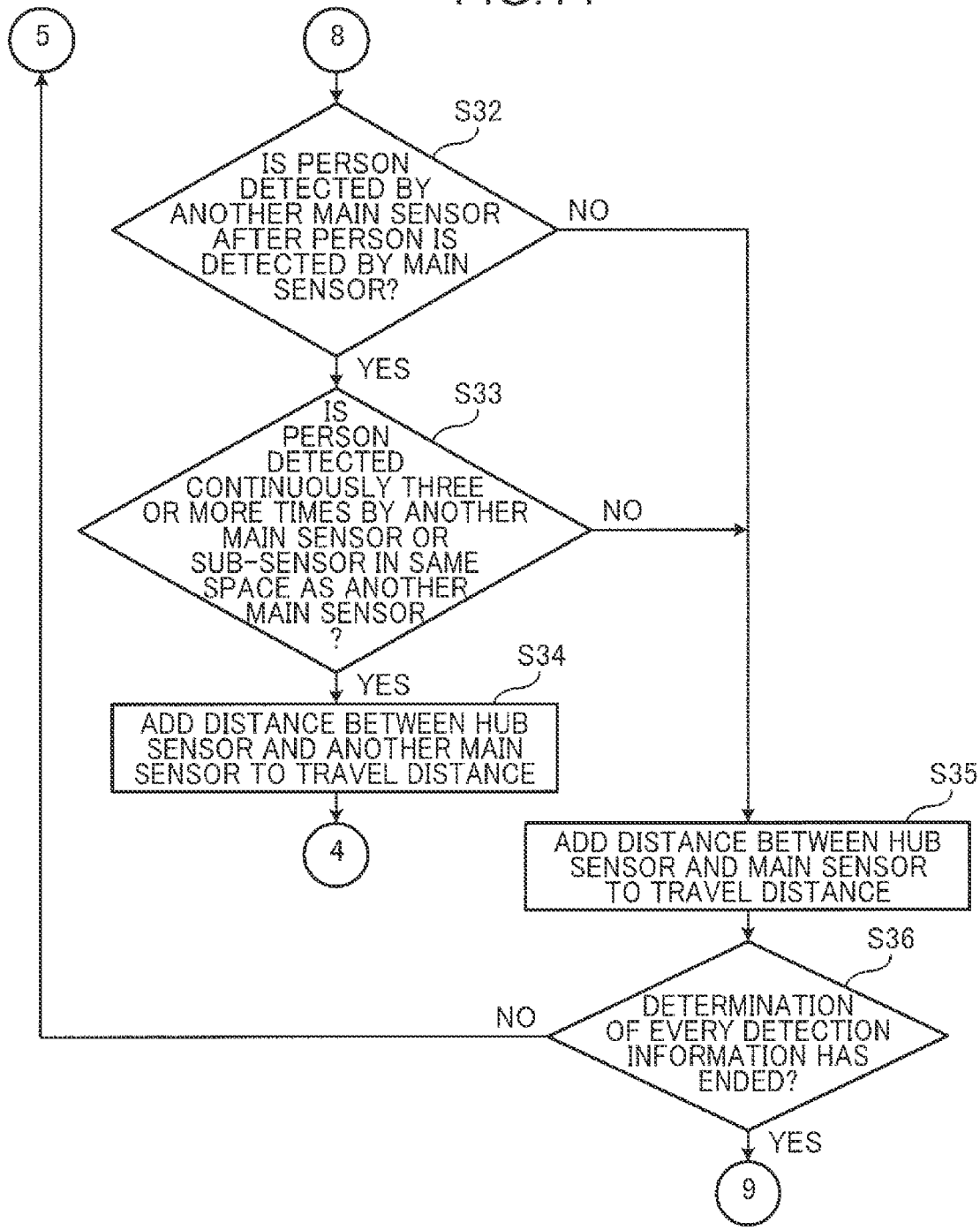
FIG. 14 is a third flowchart for illustrating travel distance calculation processing in a travel distance calculation device 2A according to the second embodiment of the present disclosure.
Figure 15:
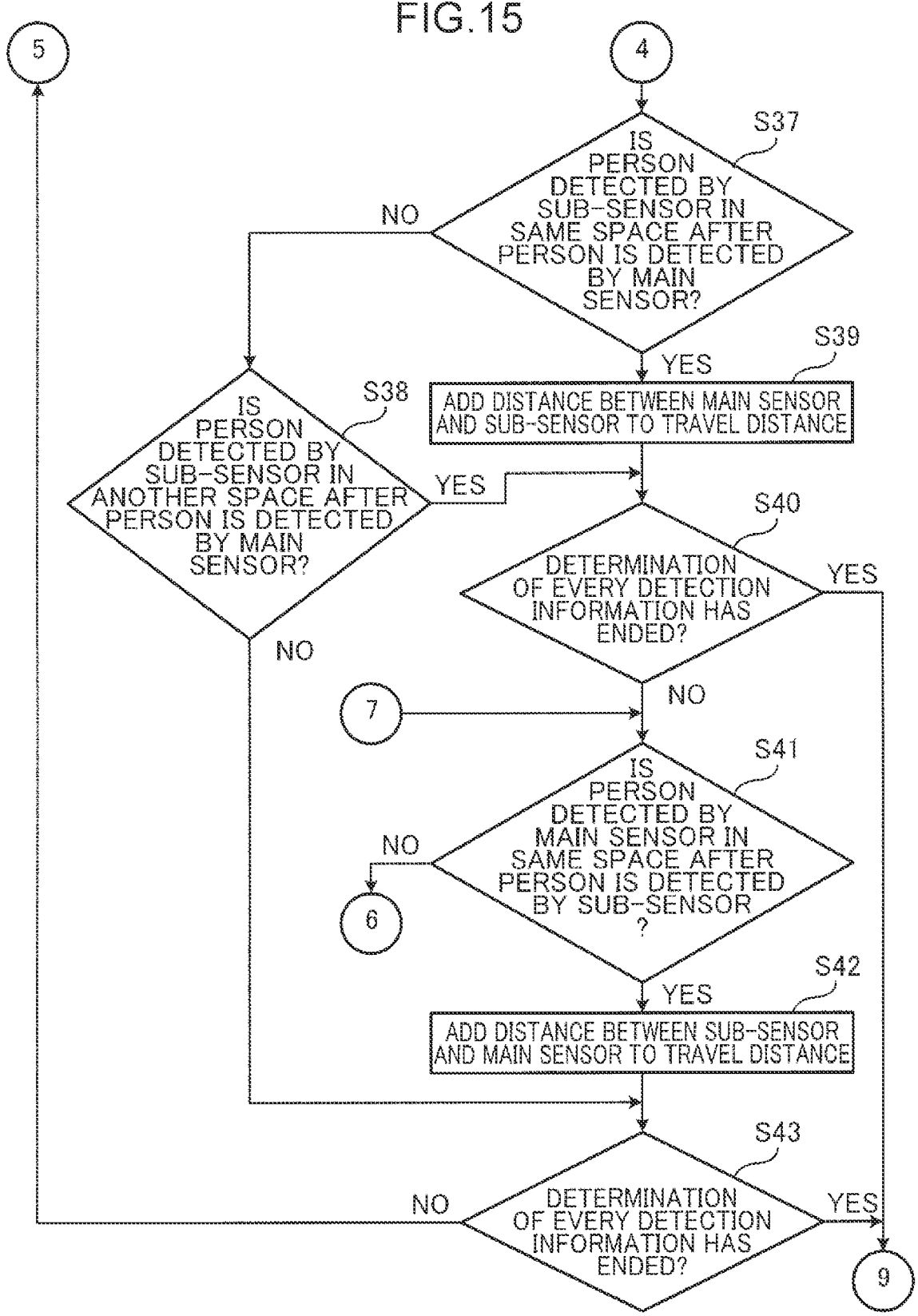
FIG. 15 is a fourth flowchart for illustrating travel distance calculation processing in the travel distance calculation device 2A according to the second embodiment of the present disclosure.
Figure 16:
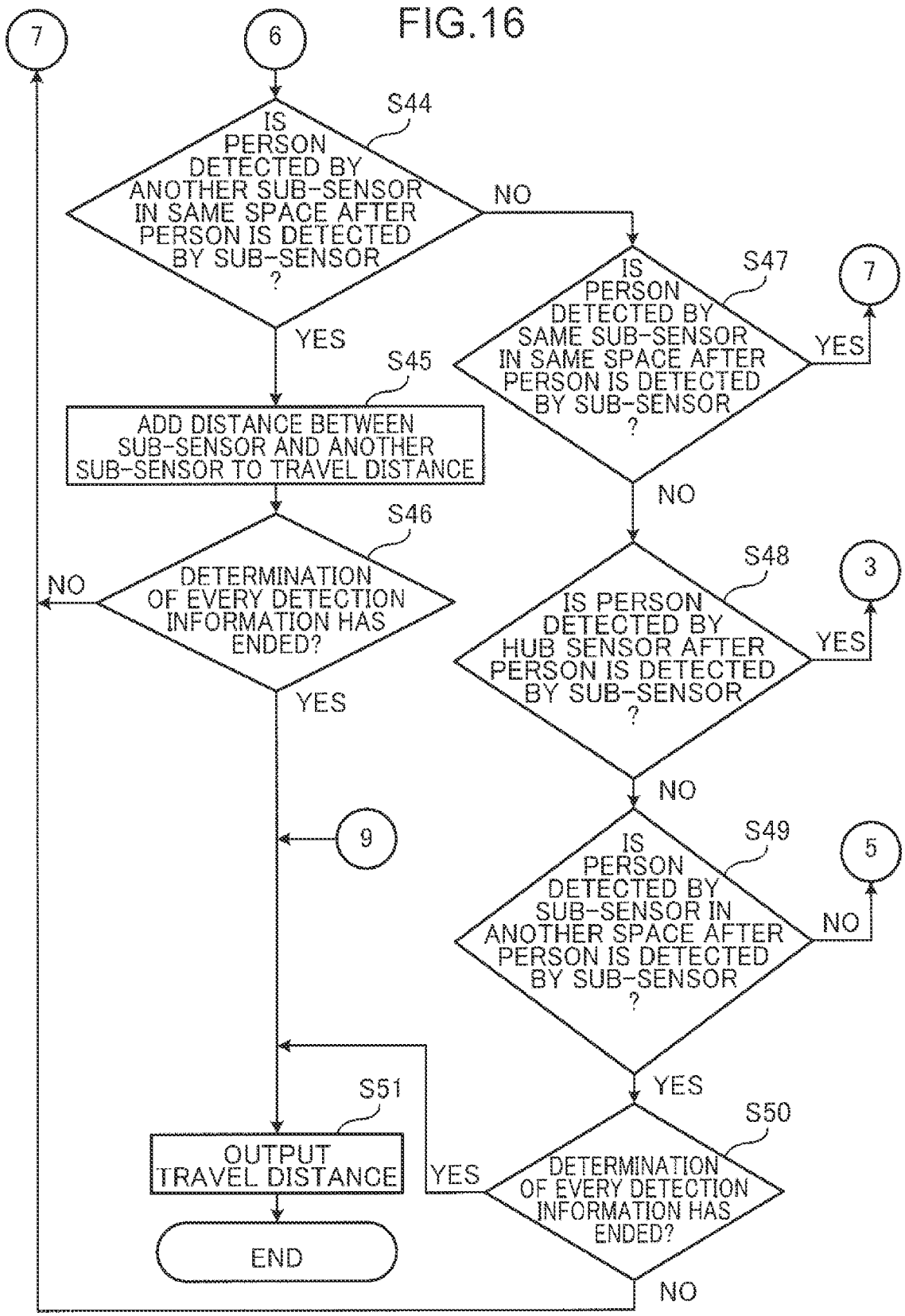
FIG. 16 is a fifth flowchart for illustrating travel distance calculation processing in the travel distance calculation device 2A according to the second embodiment of the present disclosure.

FIG. 12 is a first flowchart for illustrating travel distance calculation processing in the travel distance calculation device 2A according to the second embodiment of the present disclosure. FIG. 13 is a second flowchart for illustrating the travel distance calculation processing in the travel distance calculation device 2A according to the second embodiment of the present disclosure. FIG. 14 is a third flowchart for illustrating the travel distance calculation processing in the travel distance calculation device 2A according to the second embodiment of the present disclosure. FIG. 15 is a fourth flowchart for illustrating the travel distance calculation processing in the travel distance calculation device 2A according to the second embodiment of the present disclosure. FIG. 16 is a fifth flowchart for illustrating the travel distance calculation processing in the travel distance calculation device 2A according to the second embodiment of the present disclosure. In the following description, a main sensor MN is a general term of the first to eighth main sensors M1 to M8, and a sub-sensor SN is a general term of the sub-sensors SA1 to SA4, and SB1.

Processing in steps S21 to S22 is the same as the processing in steps S1 to S2 illustrated in FIG. 4, so that description of the processing will be omitted.

Next, the travel distance calculation unit 212A determines whether the person is first detected by the main sensor MN, in step S23. Here, when it is determined that the person is not detected by the main sensor MN first, in other words, when the person is first detected by the hub sensor H1 or the sub-sensor SN (NO in step S23), the travel distance calculation unit 212A determines whether the person is first detected by the hub sensor H1, in step S27.

When it is determined that the person is first detected by the hub sensor H1 (YES in step S27), the processing proceeds to step S28. When it is determined that the person is not detected by the hub sensor H1 first, in other words, when the person is first detected by the sub-sensor SN (NO in step S27), the processing proceeds to step S41.

In contrast, when it is determined that the person is first detected by the main sensor MN (YES in step S23), the travel distance calculation unit 212A determines whether the person is detected by the hub sensor H1 after the person is detected by the main sensor MN based on the detection information arranged in chronological order, in step S24. Here, when it is determined that the person is not detected by the hub sensor H1 after the person is detected by the main sensor MN, in other words, when it is determined that the person is detected by the main sensor MN or the sub-sensor SN after the person is detected by the main sensor MN (NO in step S24), the processing proceeds to step S37.

In contrast, when it is determined that the person is detected by the hub sensor H1 after the person is detected by the main sensor MN (YES in step S24), the travel distance calculation unit 212A adds a distance between the main sensor MN and the hub sensor H1 to the travel distance in step S25. At this time, the travel distance calculation unit 212A reads out a distance associated with a combination of an installation location of the main sensor MN and an installation location of the hub sensor H1 from the distance table stored in the distance table storage 222A, and adds the distance to the travel distance.

Next, the travel distance calculation unit 212A determines whether the determination of every detection information acquired is ended, in step S26. Then, when it is determined that the determination of every detection information acquired is ended (YES in step S26), the travel distance output unit 213 outputs the travel distance added by the travel distance calculation unit 212, in step S51. For example, the travel distance output unit 213 outputs the travel distance to the travel distance storage 223. The travel distance storage 223 stores the travel distance output by the travel distance output unit 213.

When it is determined that the determination of every detection information acquired is not ended (NO in step S26), or when it is determined that the person is first detected by the hub sensor H1 (YES in step S27), the travel distance calculation unit 212A determines whether the person is detected by the main sensor MN after the person is detected by the hub sensor H1 based on the detection information arranged in chronological order, in step S28. Here, when it is determined that the person is not detected by the main sensor MN after the person is detected by the hub sensor H1, in other words, when the person is detected by the hub sensor H1 or the sub-sensor SN after the person is detected by the hub sensor H1 (NO in step S28), the travel distance calculation unit 212A determines whether the person is detected by the sub-sensor SN after the person is detected by the hub sensor H1 based on the detection information arranged in chronological order, in step S29.

When it is determined that the person is not detected by the sub-sensor SN after the person is detected by the hub sensor H1, in other words, when the person is detected by the hub sensor H1 after the person is detected by the hub sensor H1 (NO in step S29), the travel distance calculation unit 212A determines whether the determination of every detection information acquired is ended, in step S30. Here, when it is determined that the determination of every detection information acquired is not ended (NO in step S30), the processing returns to step S28. As described above, when the person is detected continuously by the same hub sensor H1, it is estimated that the person has not traveled from a room in which the hub sensor H1 is installed. Thus, a distance between two hub sensors is not added to the travel distance.

In contrast, when it is determined that the determination of every detection information acquired is ended (YES in step S30), the processing proceeds to step S51.

When it is determined that the person is detected by the sub-sensor SN after the person is detected by the hub sensor H1 (YES in step S29), the travel distance calculation unit 212A determines whether the determination of every detection information acquired is ended, in step S31. Here, when it is determined that the determination of every detection information acquired is ended (YES in step S31), the processing proceeds to step S51.

In contrast, when it is determined that the determination of every detection information acquired is not ended (NO in step S31), the processing proceeds to step S41.

When it is determined that the person is detected by the main sensor MN after the person is detected by the hub sensor H1 (YES in step S28), the travel distance calculation unit 212A determines whether the person is detected by another main sensor MN after the person is detected by the main sensor MN based on the detection information arranged in chronological order, in step S32. That is, when the person is detected by the main sensor MN after the person is detected by the hub sensor H1, it is determined whether the person is detected by the other main sensor MN after the person is detected by the main sensor MN instead of adding the distance between the main sensor MN and the hub sensor H1 to the travel distance.

Here, when it is determined that the person is not detected by the other main sensor MN after the person is detected by the main sensor MN (NO in step S32), the travel distance calculation unit 212A adds the distance between the main sensor MN and the hub sensor H1 to the travel distance, in step S35. At this time, the travel distance calculation unit 212A reads out a distance associated with the combination of the installation location of the hub sensor H1 and the installation location of the main sensor MN from the distance table stored in the distance table storage 222A, and adds the distance to the travel distance.

Next, the travel distance calculation unit 212A determines whether the determination of every detection information acquired is ended, in step S36. Here, when it is determined that the determination of every detection information acquired is ended (YES in step S36), the processing proceeds to step S51.

In contrast, when it is determined that the determination of every detection information acquired is not ended (NO in step S36), the processing returns to step S24.

When it is determined that the person is detected by the other main sensor MN after the person is detected by the main sensor MN (YES in step S32), the travel distance calculation unit 212A determines whether the person is detected continuously three or more times by the other main sensor MN or the sub-sensor SN in the same space as the other main sensor MN based on the detection information arranged in chronological order, in step S33. Here, when it is determined that the person is not detected continuously three times or more by the other main sensor MN or the sub-sensor SN in the same space as the other main sensor MN (NO in step S33), the processing proceeds to step S35.

In contrast, when it is determined that the person is detected continuously three or more times by the other main sensor MN or the sub-sensor SN in the same space as the other main sensor MN (YES in step S33), the travel distance calculation unit 212A adds a distance between the hub sensor H1 and the other main sensor MN to the travel distance, in step S34. At this time, the travel distance calculation unit 212A reads out a distance associated with the combination of the installation location of the hub sensor H1 and the installation location of the other main sensor MN from the distance table stored in the distance table storage 222A, and adds the distance to the travel distance. In this case, the travel distance calculation unit 212A adds a distance between the hub sensor H1 and the other main sensor MN that detects the person subsequent to the main sensor MN to the travel distance instead of a distance between the hub sensor H1 and the main sensor MN that detects the person subsequent to the hub sensor H1.

When the person is detected continuously three times by the same other main sensor MN in step S33, the travel distance calculation unit 212A may add the distance between the hub sensor H1 and the other main sensor MN to the travel distance. When the person is detected continuously twice by the same sub-sensor SN in the same space as the other main sensor MN after the person is detected by the other main sensor MN in step S33, the travel distance calculation unit 212A may add the distance between the hub sensor H1 and the other main sensor MN to the travel distance.

Next, the travel distance calculation unit 212A determines whether the person is detected by the sub-sensor SN in the same space as the main sensor MN after the person is detected by the main sensor MN based on the detection information arranged in chronological order, in step S37. Here, when it is determined that the person is not detected by the sub-sensor SN in the same space as the main sensor MN after the person is detected by the main sensor MN, in other words, when the person is detected by the main sensor MN or the sub-sensor SN in another space after the person is detected by the main sensor MN (NO in step S37), the travel distance calculation unit 212A determines whether the person is detected by the sub-sensor SN in the other space after the person is detected by the main sensor MN based on the detection information arranged in chronological order, in step S38. When it is determined that the person is detected by the sub-sensor SN in the other space after the person is detected by the main sensor MN (YES in step S38), the processing proceeds to step S40.

In contrast, when it is determined that the person is not detected by the sub-sensor SN in the other space after the person is detected by the main sensor MN, in other words, when the person is detected by the main sensor MN after the person is detected by the main sensor MN (NO in step S38), the processing proceeds to step S43.

When it is determined that the person is detected by the sub-sensor SN in the same space as the main sensor MN after the person is detected by the main sensor MN (YES in step S37), the travel distance calculation unit 212A adds a distance between the main sensor MN and the sub-sensor SN to the travel distance in step S39. At this time, the travel distance calculation unit 212A reads out a distance associated with a combination of an installation location of the main sensor MN and an installation location of the sub-sensor SN from the distance table stored in the distance table storage 222A, and adds the distance to the travel distance.

Next, the travel distance calculation unit 212A determines whether the determination of every detection information acquired is ended, in step S40. Here, when it is determined that the determination of every detection information acquired is ended (YES in step S40), the processing proceeds to step S51.

In contrast, when it is determined that the determination of every detection information acquired is not ended (NO in step S40), the travel distance calculation unit 212A determines whether the person is detected by the main sensor MN in the same space as the sub-sensor SN after the person is detected by the sub-sensor SN based on the detection information arranged in chronological order, in step S41. Here, when it is determined that the person is detected by the main sensor MN in the same space as the sub-sensor SN after the person is detected by the sub-sensor SN (YES in step S41), the travel distance calculation unit 212A adds the distance between the main sensor MN and the sub-sensor SN to the travel distance in step S42. At this time, the travel distance calculation unit 212A reads out the distance associated with the combination of the installation location of the main sensor MN and the installation location of the sub-sensor SN from the distance table stored in the distance table storage 222A, and adds the distance to the travel distance.

Next, the travel distance calculation unit 212A determines whether the determination of every detection information acquired is ended, in step S43. Here, when it is determined that the determination of every detection information acquired is ended (YES in step S43), the processing proceeds to step S51.

In contrast, when it is determined that the determination of every detection information acquired is not ended (NO in step S43), the processing returns to step S24.

When it is determined that the person is not detected by the main sensor MN in the same space as the sub-sensor SN after the person is detected by the sub-sensor SN, in other words, when the person is detected by the main sensor MN in another space, another sub-sensor SN in the same space as the sub-sensor SN, the sub-sensor SN in another space, or the hub sensor H1 after the person is detected by the sub-sensor SN (NO in step S41), the travel distance calculation unit 212A determines whether the person is detected by the other sub-sensor SN in the same space as the sub-sensor SN after the person is detected based on the detection information arranged in chronological order, in step S44. Here, when it is determined that the person is detected by the other sub-sensor SN in the same space as the sub-sensor SN after the person is detected by the sub-sensor SN (YES in step S44), the travel distance calculation unit 212A adds a distance between the sub-sensor SN and the other sub-sensor SN to the travel distance, in step S45. At this time, the travel distance calculation unit 212A reads out the distance associated with the combination of the installation location of the sub-sensor SN and an installation location of the other sub-sensor SN from the distance table stored in the distance table storage 222A, and adds the distance to the travel distance.

Next, the travel distance calculation unit 212A determines whether the determination of every detection information acquired is ended, in step S46. Here, when it is determined that the determination of every detection information acquired is ended (YES in step S46), the processing proceeds to step S51.

In contrast, when it is determined that the determination of every detection information acquired is not ended (NO in step S46), the processing returns to step S41.

When it is determined that the person is not detected by the other sub-sensor SN in the same space as the sub-sensor SN after the person is detected by the sub-sensor SN, in other words, when the person is detected by the sub-sensor SN that is the same and in the same space as the sub-sensor SN by which the person is detected before, the main sensor MN in another space, the sub-sensor SN in another space, or the hub sensor H1 after the person is detected by the sub-sensor SN (NO in step S44), the travel distance calculation unit 212A determines whether the person is detected by the sub-sensor SN that is the same and in the same space as the sub-sensor SN by which the person is detected before based on the detection information arranged in chronological order, in step S47. Here, when it is determined that the person is detected by the sub-sensor SN that is the same and in the same space as the sub-sensor SN by which the person is detected before (YES in step S47), the processing returns to step S41. That is, when the person is detected continuously by the same sub-sensor SN, it is estimated that the person has not traveled, and thus the processing returns to step S41 by adding no distance.

In contrast, when it is determined that the person is not detected by the sub-sensor SN that is the same and in the same space as the sub-sensor SN by which the person is detected before, in other words, when the person is detected by the main sensor MN in another space, the sub-sensor SN in another space, or the hub sensor H1 after the person is detected by the sub-sensor SN (NO in step S47), the travel distance calculation unit 212A determines whether the person is detected by the hub sensor H1 after the person is detected by the sub-sensor SN based on the detection information arranged in chronological order, in step S48. Here, when it is determined that the person is detected by the hub sensor H1 after the person is detected by the sub-sensor SN (YES in step S48), the processing returns to step S28.

Then, when it is determined that the person is not detected by the hub sensor H after the person is detected by the sub-sensor SN, in other words, when the person is detected by the main sensor MN in another space or the sub-sensor SN in the other space after the person is detected by the sub-sensor SN (NO in step S48), the travel distance calculation unit 212A determines whether the person is detected by the sub-sensor SN in the other space after the person is detected by the sub-sensor SN based on the detection information arranged in chronological order, in step S49. Here, when it is determined that the person is not detected by the sub-sensor SN in the other space after the person is detected by the sub-sensor SN, in other words, when the person is detected by the main sensor MN in the other space after the person is detected by the sub-sensor SN (NO in step S49), the processing returns to step S24.

When it is determined that the person is detected by the sub-sensor SN in the other space after the person is detected by the sub-sensor SN (YES in step S49), it is determined whether the determination of every detection information acquired is ended, in step S50. Here, when it is determined that the determination of every detection information acquired is ended (YES in step S50), the processing proceeds to step S51.

In contrast, when it is determined that the determination of every detection information acquired is not ended (NO in step S50), the processing returns to step S41.

Figure 17:
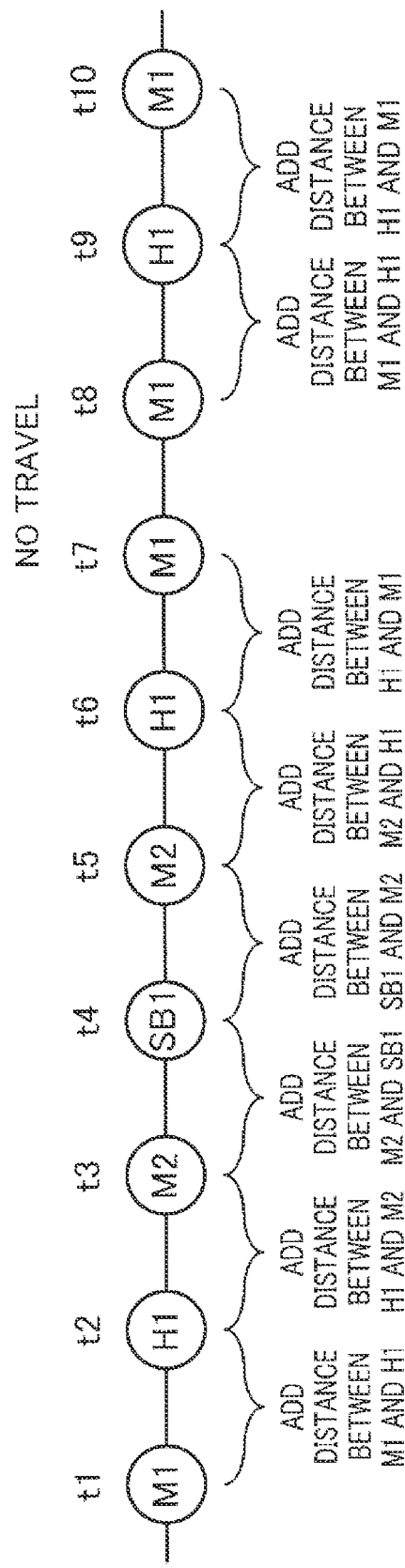
FIG. 17 is a diagram illustrating the main sensor, the hub sensor, the sub-sensor that output detection information and that are arranged in chronological order when the main sensor, the hub sensor, and the sub-sensor normally detect a person in the second embodiment.

FIG. 17 is a diagram illustrating the main sensor, the hub sensor, the sub-sensor that output detection information and that are arranged in chronological order when the main sensor, the hub sensor, and the sub-sensor normally detect the person in the second embodiment.

First, the hub sensor H1 detects the person at time t2 after the first main sensor M1 detects the person at time t1, so that the first distance between the first main sensor M1 and the hub sensor H1 is added to the travel distance. Then, the second main sensor M2 detects the person at time t3 after the hub sensor H1 detects the person at time t2, so that the second distance between the second main sensor M2 and the hub sensor H1 is added to the travel distance. After the second main sensor M2 detects the person at time t3, the sub-sensor SB1 installed in the same space as the second main sensor M2 detects the person at time t4. Thus, the distance between the second main sensor M2 and the sub-sensor SB1 is added to the travel distance.

Then, the second main sensor M2 detects the person at time t5 after the sub-sensor SB1 detects the person at time t4, so that the distance between the second main sensor M2 and the sub-sensor SB1 is added to the travel distance. The hub sensor H1 detects the person at time t6 after the second main sensor M2 detects the person at time t5, so that the second distance between the second main sensor M2 and the hub sensor H1 is added to the travel distance.

Then, the first main sensor M1 detects the person at time t7 after the hub sensor H1 detects the person at time t6, so that the first distance between the first main sensor M1 and the hub sensor H1 is added to the travel distance. Then, the first main sensor M1 detects the person at time t8 after the first main sensor M1 detects the person at time t7, so that the distance between the first main sensor M1 at the former detection and the first main sensor M1 at the latter detection is not added to the travel distance. This is because it is estimated that the person has not traveled from the first space 101.

The hub sensor H1 detects the person at time t9 after the first main sensor M1 detects the person at time t8, so that the first distance between the first main sensor M1 and the hub sensor H1 is added to the travel distance. Then, the first main sensor M1 detects the person at time t10 after the hub sensor H1 detects the person at time t9, so that the first distance between the first main sensor M1 and the hub sensor H1 is added to the travel distance.

Figure 18:
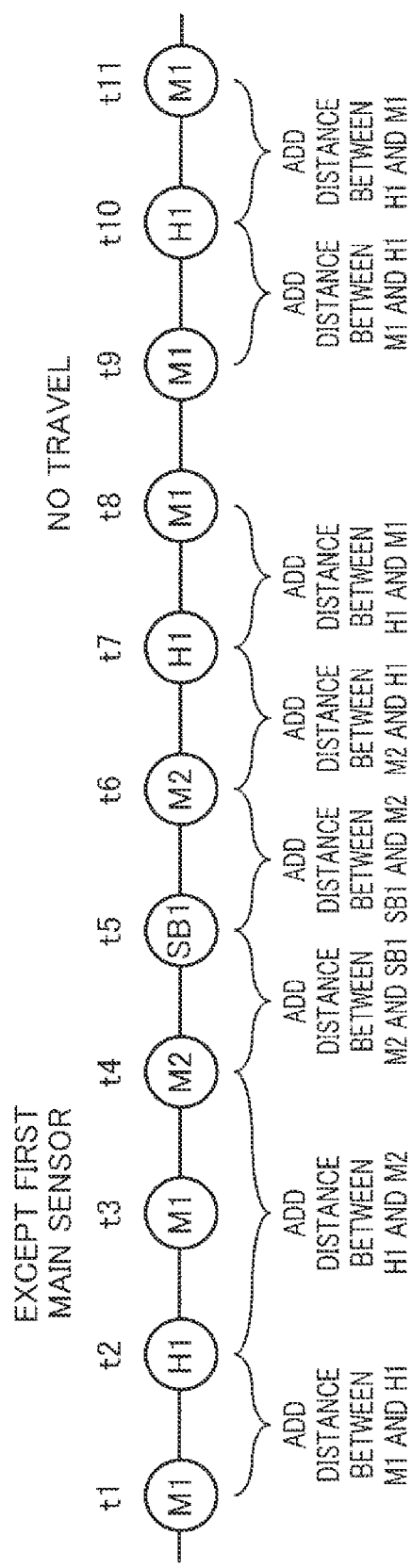
FIG. 18 is a diagram illustrating the main sensor, the hub sensor, and the sub-sensor that output detection information and that are arranged in chronological order when the main sensor erroneously detect the person in the second embodiment.

FIG. 18 is a diagram illustrating the main sensor, the hub sensor, and the sub-sensor that output detection information and that are arranged in chronological order when the main sensor erroneously detect the person in the second embodiment.

First, the hub sensor H1 detects the person at time t2 after the first main sensor M1 detects the person at time t1, so that the first distance between the first main sensor M1 and the hub sensor H1 is added to the travel distance. Then, the first main sensor M1 detects the person at time t3 after the hub sensor H1 detects the person at time 2. However, it is not known whether the first main sensor M1 has correctly detected the person, so that the first distance between the first main sensor M1 and the hub sensor H1 is not added to the travel distance at this time.

Next, the second main sensor M2 detects the person at time t4 after the first main sensor M1 detects the person at time t3. Then, the sub-sensor SB1 installed in the same space as the second main sensor M2 detects the person at time t5, and the second main sensor M2 detects the person at time t6. That is, the second main sensor M2, the sub-sensor SB1 in the second space 102, and the second main sensor M2 continuously detect the person after the first main sensor M1 detects the person, so that it can be estimated that the person has not traveled from the third space 103 to the first space 101 but has traveled from the third space 103 to the second space 102. As described above, at least one of the second main sensor M2 and the sub-sensor SB1 in the second space 102 continuously detects the person three or more times after the first main sensor M1 detects the person, the second distance between the second main sensor M2 and the hub sensor H1 is added to the travel distance instead of the first distance between the first main sensor M1 and the hub sensor H1. As a result, the travel distance of the person can be calculated more accurately even when a sensor reacts erroneously.

When the person is detected continuously at least three times by sub-sensors installed in the second space 102 after the person is detected by the first main sensor M1 installed in the first space 101, the travel distance calculation unit 212A may add the second distance between the second main sensor M2 installed in the second space 102 and the hub sensor H1 to the travel distance by estimating that the person is in the second space 102. The sub-sensors having continuously detected the person at least three times may include the same sub-sensor or may include sub-sensors different from each other.

In each of the above embodiments, each component may be configured by dedicated hardware, or may be implemented by executing a software program suitable for each component. Each component may be implemented by a program execution unit such as a CPU or a processor reading and executing a software program recorded on a recording medium such as a hard disk or a semiconductor memory. Alternatively, the program may be executed by another independent computer system by recording and transferring the program on a recording medium or transferring the program via a network.

Some or all of functions of the devices according to the embodiments of the present disclosure are typically realized as a large scale integration (LSI) that is an integrated circuit. The functions may be individually integrated into one chip, or may be integrated into one chip including some or all of the functions. The integrated circuit is not limited to the LSI, and may be realized by a dedicated circuit or a general-purpose processor. A field programmable gate array (FPGA) that can be programmed after manufacturing an LSI, or a reconfigurable processor that can reconfigure connection and setting of circuit cells inside an LSI, may be used.

Additionally, some or all of functions of the devices according to the embodiments of the present disclosure may be implemented by a processor such as a CPU executing a program.

The numbers used above are merely examples for specifically describing the present disclosure, and the present disclosure is not limited to the illustrated numbers.

The order in which the steps shown in the above flowcharts are performed is merely an example for specifically describing the present disclosure, and any order other than the above may be available as long as a similar effect can be obtained. Some of the above steps may be performed simultaneously (in parallel) with another step.

INDUSTRIAL APPLICABILITY

The technique according to the present disclosure is useful for a technique for calculating a travel distance of a person in a house because the travel distance of a person can be calculated even when a sensor reacts erroneously.

The invention claimed is:

1. A travel distance calculation method used in a travel distance calculation device that calculates a travel distance of a person in a house, the travel distance calculation method comprising:

acquiring first detection information indicating that the person is detected by a first sensor provided in a first space in the house, second detection information indicating that the person is detected by a second sensor provided in a second space different from the first space in the house, third detection information indicating that the person is detected by a third sensor provided in a third space connecting the first space and the second space in the house, and fourth detection information indicating that the person is detected by a fourth sensor provided at a position different from a position where the first sensor is provided in the first space;

adding a first distance between the first sensor and the third sensor to the travel distance based on the first detection information and the third detection information when the person is detected by the third sensor after the person is detected by the first sensor or when the person is detected by the first sensor after the person is detected by the third sensor, adding a second distance between the second sensor and the third sensor to the travel distance based on the second detection information and the third detection information when the person is detected by the third sensor after the person is detected by the second sensor or when the person is detected by the second sensor after the person is detected by the third sensor, adding no third distance between the first sensor and the second sensor to the travel distance based on the first detection information and the second detection information when the person is detected by the second sensor after the person is detected by the first sensor or when the person is detected by the first sensor after the person is detected by the second sensor, adding a fourth distance between the first sensor and the fourth sensor to the travel distance based on the first detection information and the fourth detection information when the person is detected by the fourth sensor after the person is detected by the first sensor or when the person is detected by the first sensor after the person is detected by the fourth sensor, and adding the first distance between the first sensor and the third sensor to the travel distance without adding the second distance between the second sensor and the third sensor to the travel distance when the person is detected by the second sensor after the person is detected by the third sensor, the person is detected by the first sensor after the person is detected by the second sensor, and the person is detected continuously three or more times by at least one of the first sensor and the fourth sensor after the person is detected by the first sensor; and outputting the added travel distance.

2. The travel distance calculation method according to claim 1 wherein when the person is detected by the third sensor after the person is detected by the first sensor or when the person is detected by the first sensor after the person is detected by the third sensor, the first distance associated with a first combination of an installation location of the first sensor and an installation location of the third sensor is read out from a table to add the first distance to the travel distance, the table being configured to associate the first combination of the installation location of the first sensor and the installation location of the third sensor with the first distance between the first sensor and the third sensor, and a second combination of an installation location of the second sensor and the installation location of the third sensor with the second distance between the second sensor and the third sensor, and when the person is detected by the third sensor after the person is detected by the second sensor or when the person is detected by the second sensor after the person is detected by the third sensor, the second distance associated with the second combination of the installation location of the second sensor and the installation location of the third sensor is read out from the table to add the second distance to the travel distance.

3. The travel distance calculation method according to claim 1, wherein the travel distance is not calculated when the person is detected simultaneously by any two of the first sensor, the second sensor, and the third sensor.

4. A travel distance calculation device configured to calculate a travel distance of a person in a house, the travel distance calculation device comprising:

an acquisition unit that acquires first detection information indicating that the person is detected by a first sensor provided in a first space in the house, second detection information indicating that the person is detected by a second sensor provided in a second space different from the first space in the house, third detection information indicating that the person is detected by a third sensor provided in a third space connecting the first space and the second space in the house, and fourth detection information indicating that the person is detected by a fourth sensor provided at a position different from a position where the first sensor is provided in the first space;

a travel distance calculation unit that adds a first distance between the first sensor and the third sensor to the travel distance based on the first detection information and the third detection information when the person is detected by the third sensor after the person is detected by the first sensor or when the person is detected by the first sensor after the person is detected by the third sensor, and that adds a second distance between the second sensor and the third sensor to the travel distance based on the second detection information and the third detection information when the person is detected by the third sensor after the person is detected by the second sensor or when the person is detected by the second sensor after the person is detected by the third sensor, and that adds no third distance between the first sensor and the second sensor to the travel distance based on the first detection information and the second detection information when the person is detected by the second sensor after the person is detected by the first sensor or when the person is detected by the first sensor after the person is detected by the second sensor, and that adds a fourth distance between the first sensor and the fourth sensor to the travel distance based on the first detection information and the fourth detection information when the person is detected by the fourth sensor after the person is detected by the first sensor or when the person is detected by the first sensor after the person is detected by the fourth sensor, and that adds the first distance between the first sensor and the third sensor to the travel distance without adding the second distance between the second sensor and the third sensor to the travel distance when the person is detected by the second sensor after the person is detected by the third sensor, the person is detected by the first sensor after the person is detected by the second sensor, and the person is detected continuously three or more times by at least one of the first sensor and the fourth sensor after the person is detected by the first sensor; and an output unit that outputs the added travel distance.

5. A non-transitory computer readable recording medium storing a travel distance calculation program that is configured to calculate a travel distance of a person in a house, the program causing a computer to function so as to:

acquire first detection information indicating that the person is detected by a first sensor provided in a first space in the house, second detection information indicating that the person is detected by a second sensor provided in a second space different from the first space in the house, third detection information indicating that the person is detected by a third sensor provided in a third space connecting the first space and the second space in the house, and fourth detection information indicating that the person is detected by a fourth sensor provided at a position different from a position where the first sensor is provided in the first space;

add a first distance between the first sensor and the third sensor to the travel distance based on the first detection information and the third detection information when the person is detected by the third sensor after the person is detected by the first sensor or when the person is detected by the first sensor after the person is detected by the third sensor, add a second distance between the second sensor and the third sensor to the travel distance based on the second detection information and the third detection information when the person is detected by the third sensor after the person is detected by the second sensor or when the person is detected by the second sensor after the person is detected by the third sensor, add no third distance between the first sensor and the second sensor to the travel distance based on the first detection information and the second detection information when the person is detected by the second sensor after the person is detected by the first sensor or when the person is detected by the first sensor after the person is detected by the second sensor, add a fourth distance between the first sensor and the fourth sensor to the travel distance based on the first detection information and the fourth detection information when the person is detected by the fourth sensor after the person is detected by the first sensor or when the person is detected by the first sensor after the person is detected by the fourth sensor, and add the first distance between the first sensor and the third sensor to the travel distance without adding the second distance between the second sensor and the third sensor to the travel distance when the person is detected by the second sensor after the person is detected by the third sensor, the person is detected by the first sensor after the person is detected by the second sensor, and the person is detected continuously three or more times by at least one of the first sensor and the fourth sensor after the person is detected by the first sensor; and output the added travel distance.

* * * * *